(12) United States Patent
Sullivan et al.

(10) Patent No.: US 8,020,433 B2
(45) Date of Patent: Sep. 20, 2011

(54) SYSTEMS AND METHODS FOR A SAMPLE FLUID COLLECTION DEVICE

(75) Inventors: Benjamin Sullivan, San Diego, CA (US); Steve Zmina, San Diego, CA (US); Eric Donsky, San Diego, CA (US); Sasha Miu, West Brunswick (AU); Graeme John Bullock, Doncaster (AU); Adam Ernest Donath, Kew (AU); Fred Harry Davis, Canterbury (AU); Andreas Knaack, Elsternwick (AU); Matthew Daniel Solomon, Hughesdale (AU); Erol Craig Harvey, Ringwood North (AU); Carl Gang Chen, Hawthorn (AU)

(73) Assignee: Tearlab Research, Inc., San Diego, CA (US)

( * ) Notice: Subject to any disclaimer, the term of this patent is extended or adjusted under 35 U.S.C. 154(b) by 397 days.

(21) Appl. No.: 12/058,428

(22) Filed: Mar. 28, 2008

(65) Prior Publication Data
US 2008/0264151 A1    Oct. 30, 2008

Related U.S. Application Data

(63) Continuation-in-part of application No. 12/001,243, filed on Dec. 11, 2007, now Pat. No. 7,810,380, and a continuation-in-part of application No. 10/400,617, filed on Mar. 25, 2003, now Pat. No. 7,017,394.

(60) Provisional application No. 60/908,654, filed on Mar. 28, 2007, provisional application No. 60/869,543, filed on Dec. 11, 2006.

(51) Int. Cl.
*G01N 13/04* (2006.01)

(52) U.S. Cl. .................................. 73/64.47

(58) Field of Classification Search ............... 73/64.47
See application file for complete search history.

(56) References Cited

U.S. PATENT DOCUMENTS

| 4,028,931 A | 6/1977 | Bisera et al. |
| 4,150,564 A | 4/1979 | Barlow et al. |
| 4,245,495 A | 1/1981 | Kakiuchi et al. |
| 4,269,197 A | 5/1981 | Gilbard |

(Continued)

FOREIGN PATENT DOCUMENTS

DE    3414866 A1    10/1985
(Continued)

OTHER PUBLICATIONS

International Search Report for PCT/US08/58731 mailed Jul. 11, 2008.
Chandler, D.E. et al., "Detection of Calcium Signals in Neutrophils Using Fluorescent Dyes," Luminescence Applications 383:70-83 (1989).
Mitsubiyashi, K. et al., "Flexible Conductimetric Sensor," Anal. Chem. 65:3586-3590 (1993).

(Continued)

*Primary Examiner* — Hezron Williams
*Assistant Examiner* — Rodney T Frank
(74) *Attorney, Agent, or Firm* — Wilson Sonsini Goodrich & Rosati

(57) ABSTRACT

A fluid collection device comprising a body comprising a capsule interface, and a capsule configured to interface with the body via the capsule interface and configured to hold a sample receiving chip. The sample receiving chip comprises a substrate that receives an aliquot volume of a sample fluid, wherein the substrate is operatively shaped to receive the aliquot volume of sample fluid through capillary action, and a sample region of the substrate, sized such that the volume of the sample fluid is sufficient to operatively cover a portion of the sample region, whereupon energy properties of the sample fluid can be transduced to produce a sample fluid reading.

24 Claims, 34 Drawing Sheets

U.S. PATENT DOCUMENTS

| | | |
|---|---|---|
| 4,305,823 A | 12/1981 | Batzer et al. |
| 4,455,864 A | 6/1984 | Wallner |
| 4,475,556 A | 10/1984 | Reiff |
| 4,603,699 A | 8/1986 | Himpens |
| 4,706,495 A | 11/1987 | Steudle et al. |
| 4,787,963 A | 11/1988 | MacConnell |
| 4,951,683 A | 8/1990 | Davis |
| 4,996,993 A | 3/1991 | York |
| 5,005,403 A | 4/1991 | Steudle et al. |
| 5,132,012 A | 7/1992 | Miura et al. |
| 5,143,080 A | 9/1992 | York |
| 5,211,055 A | 5/1993 | Steudle et al. |
| 5,218,088 A | 6/1993 | Gorenstein et al. |
| 5,230,864 A | 7/1993 | Columbus |
| 5,388,449 A | 2/1995 | LeVeen et al. |
| 5,461,699 A | 10/1995 | Arbabi et al. |
| 5,571,568 A | 11/1996 | Ribi et al. |
| 5,591,636 A | 1/1997 | Grass |
| 5,605,662 A | 2/1997 | Heller et al. |
| 5,620,584 A | 4/1997 | Reetz et al. |
| 5,665,904 A | 9/1997 | Boling |
| 5,739,376 A | 4/1998 | Bingel |
| 5,766,435 A | 6/1998 | Liao et al. |
| 5,810,725 A | 9/1998 | Sugihara et al. |
| 5,849,208 A | 12/1998 | Hayes et al. |
| 5,849,486 A | 12/1998 | Heller et al. |
| 5,851,489 A | 12/1998 | Wolf et al. |
| 5,869,231 A | 2/1999 | Romisch et al. |
| 5,994,410 A | 11/1999 | Chiang et al. |
| 5,997,817 A | 12/1999 | Crismore et al. |
| 6,048,690 A | 4/2000 | Heller et al. |
| 6,162,926 A | 12/2000 | Murphy et al. |
| 6,183,714 B1 | 2/2001 | Smalley et al. |
| 6,224,550 B1 | 5/2001 | Ellingsen |
| 6,344,272 B1 | 2/2002 | Oldenburg et al. |
| 6,403,317 B1 | 6/2002 | Anderson |
| 6,529,277 B1 | 3/2003 | Weitekamp |
| 6,558,945 B1 | 5/2003 | Kao |
| 6,583,220 B1 | 6/2003 | Lipman |
| 6,602,400 B1 | 8/2003 | Choong et al. |
| 6,630,307 B2 | 10/2003 | Bruchez et al. |
| 6,682,895 B2 | 1/2004 | Mirkin et al. |
| 6,740,518 B1 | 5/2004 | Duong et al. |
| 6,750,016 B2 | 6/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,778,316 B2 | 8/2004 | Halas et al. |
| 6,884,356 B2 | 4/2005 | Kosenka et al. |
| 6,894,511 B2 | 5/2005 | Yukimasa et al. |
| 7,017,394 B2 | 3/2006 | Sullivan |
| 7,021,122 B1 | 4/2006 | Rosenberg et al. |
| 7,051,569 B2 | 5/2006 | Sullivan |
| 7,111,502 B2 | 9/2006 | Sullivan et al. |
| 7,127,957 B2 | 10/2006 | Mathur et al. |
| 7,133,712 B2 | 11/2006 | Cohan et al. |
| 7,204,122 B2 | 4/2007 | Sullivan et al. |
| 7,344,679 B2 | 3/2008 | Natarajan et al. |
| 7,449,307 B2 | 11/2008 | Cima et al. |
| 7,574,902 B2 | 8/2009 | Sullivan |
| 2002/0031813 A1 | 3/2002 | Ozkan et al. |
| 2002/0182627 A1 | 12/2002 | Wang et al. |
| 2003/0013109 A1 | 1/2003 | Ballinger et al. |
| 2003/0054342 A1 | 3/2003 | Star et al. |
| 2003/0143580 A1 | 7/2003 | Straus |
| 2004/0023415 A1 | 2/2004 | Sokolov et al. |
| 2004/0036485 A1 | 2/2004 | Sullivan |
| 2004/0086897 A1 | 5/2004 | Mirkin et al. |
| 2004/0099813 A1 | 5/2004 | Eggeling et al. |
| 2004/0110220 A1 | 6/2004 | Mirkin et al. |
| 2004/0146918 A1 | 7/2004 | Weiner et al. |
| 2004/0147031 A1 | 7/2004 | Nakao |
| 2004/0220089 A1 | 11/2004 | Ellis et al. |
| 2005/0032204 A1 | 2/2005 | Rodgers et al. |
| 2005/0104606 A1 | 5/2005 | Donsky |
| 2005/0106714 A1 | 5/2005 | Zarur et al. |
| 2005/0239116 A1 | 10/2005 | Willey |
| 2005/0255453 A1 | 11/2005 | Qian et al. |
| 2006/0107729 A1 | 5/2006 | Sullivan et al. |
| 2006/0137435 A1 | 6/2006 | Sullivan |
| 2006/0141469 A1 | 6/2006 | Rossier et al. |
| 2007/0086927 A1 | 4/2007 | Natarajan et al. |
| 2008/0050282 A1 | 2/2008 | Natarajan et al. |
| 2008/0053206 A1 | 3/2008 | Natarajan et al. |
| 2008/0057569 A1 | 3/2008 | Natarajan et al. |
| 2008/0103376 A1 | 5/2008 | Felder |
| 2008/0273171 A1 | 11/2008 | Xu et al. |
| 2008/0286750 A1 | 11/2008 | Xu et al. |

FOREIGN PATENT DOCUMENTS

| | | |
|---|---|---|
| EP | 0391674 A2 | 10/1990 |
| EP | 0571066 A2 | 11/1993 |
| JP | 63-096455 | 4/1988 |
| JP | 6-296595 | 10/1994 |
| JP | 7-506431 | 7/1995 |
| JP | 07-239313 | 9/1995 |
| JP | 2002-176999 A | 6/2002 |
| WO | WO-87-00286 A1 | 1/1987 |
| WO | WO-93-22054 A1 | 11/1993 |
| WO | WO-96-14571 A1 | 5/1996 |
| WO | WO-98-38334 A1 | 9/1998 |
| WO | WO-99-23938 A1 | 5/1999 |
| WO | WO-01-53798 A1 | 7/2001 |
| WO | WO-01-83674 A1 | 11/2001 |
| WO | WO-02-103354 A1 | 12/2002 |
| WO | WO-2004-017050 A1 | 2/2004 |
| WO | WO-2005-076796 A3 | 2/2005 |
| WO | WO-2005-076796 A2 | 8/2005 |
| WO | WO-2008-73399 A1 | 6/2008 |

OTHER PUBLICATIONS

Papageorgion, G. et al., "A sensitive method for the estimation of the cytoplasmic osmolality of cyanobacterial cells using chlorophyll *a* fluorescence," Biochim. Biophysica Acta 1335:1-4 (1997).

Bhanot et al., "The Importance of Thermodynamic Equilibrium for High Throughput Gene Expression Arrays," Biophysical J. 84:124-135 (2003).

BIOSIS abstract #002246922, Claudino et al., "The role of cGMP on uroguanylin responses in salt-loaded rats," Annual Meeting of Professional Research Scientists on Experimental Biology, New Orleans, LA, USA< Apr. 20-24, 2002; FASEB J 16:A956 Mar. 22, 2002.

Borisenko et al., "Simultaneous Optical and Electrical Recording of Single Gramicidin Channels," Biophysical J. 84(1):612-622 (2003).

Braun et al., "Lock-in by molecular multiplication," Applied Physics Ltrs 83(26):5554-5556 (2003).

Farris, "Tear Osmolarity—A New Gold Standard," 1994, pp. 495-503.

Fritzche et al., "Metal nanoparticles as labels or heterogenous, chip-based DNA detection," Nanotechnology 14(12):R63-R73, (2003).

Geerling et al., "Quality of salivary tears following autologous submandibular gland transplantation for severe dry eye," Graefe's Arch Clin Exp Opthalmol 238:45-52 (2000).

Kung et al., "Adaptive Principal Component Extraction (APEX) and Applications," IEEE Transactions on signal Processing 42(5):1202-1217 (1994).

Ogasawara et al., "Electrical conductivity of tear fluid in healthy persons and keratoconjunctivitis siccs patients measured by a flexible conductimetric sensor," Graefe's Arch Clin Exp Ophthalmol 234:542-546 (1996).

Pensyl et al., "Vapor Pressure Osmometry: Minimum Sample Microvolumes," Acta Ophthalmol Scan 77(1):27-30 (1999).

Vollmer et al., "Multiplexed DNA Quantification by Spectroscopic Shift of Two Microsphere Cavities," Biophysical .Journal 85:1974-1979 (2003).

EP 04795939.0 Supplementary Partial Search Report mailed Feb. 28, 2007.

PCT/US05/01573 Search Report mailed Mar. 6, 2006.

PCT/US07/25277 Search Report mailed May 13, 2008.

PCT/US03/09553 Search Report mailed Oct. 10, 2003.

SYSTEMS AND METHODS FOR A SAMPLE FLUID COLLECTION DEVICE

RELATED APPLICATIONS INFORMATION

This application claims priority under 35 U.S.C. 119(e) to U.S. Provisional Patent Application Ser. No. 60/908,654, filed Mar. 28, 2007 and entitled "Systems and Methods for Collecting and Analyzing Tears Using a Pen Type Device," which is incorporated herein by reference as if set forth in full.

This application also claims priority as a Continuation-In-Part under 35 U.S.C. 120 to U.S. utility patent application Ser. No. 12/001,243, filed Dec. 11, 2007 and entitled "Systems and Methods for Collecting Tear Film and Measuring Tear Film Osmolarity", now U.S. Pat. No. 7,810,380, which in turn claims priority under 35 U.S.C. 119(e) to U.S. Provisional Patent Application Ser. No. 60/869,543, filed Dec. 11, 2006 and entitled "Systems and Methods for Collecting Tear Film and Measuring Tear Film Osmolarity," and as a Continuation-In-Part under 35 U.S.C. 120 of U.S. patent application Ser. No. 10/400,617 filed Mar. 25, 2003 and entitled "Tear Film Osmometer", now U.S. Pat. No. 7,017,394, which claims priority to U.S. Provisional Patent Application Ser. No. 60/401,432 entitled "Volume Independent Tear Film Osmometer" filed Aug. 6, 2002. Each of these applications is incorporated herein by reference as if set forth in full.

BACKGROUND

1. Technical Field

The embodiments described herein relate generally to measuring the osmotic pressure of fluids and, more particularly, to collecting tear film for measuring the osmolarity of tear film using an ergonomic tear collection device with superior tear collection properties.

2. Related Art

Tears fulfill an essential role in maintaining ocular surface integrity, protecting against microbial challenge, and preserving visual acuity. These functions, in turn, are critically dependent upon the composition and stability of the tear film structure, which includes an underlying mucin foundation, a middle aqueous component, and an overlying lipid layer. Disruption, deficiency, or absence of the tear film can severely impact the eye. If unmanaged with artificial tear substitutes or tear film conservation therapy, these disorders can lead to intractable desiccation of the corneal epithelium, ulceration and perforation of the cornea, an increased incidence of infectious disease, and ultimately pronounced visual impairment and blindness.

Keratoconjunctivitis sicca (KCS), or "dry eye", is a condition in which one or more of the tear film structure components listed above is present in insufficient volume or is otherwise out of balance with the other components. It is known that the fluid tonicity or osmolarity of tears increases in patients with KCS. KCS is associated with conditions that affect the general health of the body, such as Sjogren's syndrome, aging, and androgen deficiency. Therefore, osmolarity of a tear film can be a sensitive and specific indicator for the diagnosis of KCS and other conditions.

The osmolarity of a sample fluid, e.g., a tear, can be determined by an ex vivo technique called "freezing point depression," in which solutes or ions in a solvent, i.e. water, cause a lowering of the fluid freezing point from what it would be without the ions. In freezing point depression analysis, the freezing point of the ionized sample fluid is found by detecting the temperature at which a quantity of the sample, typically on the order of about several milliliters, first begins to freeze in a container, e.g., a tube. To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. The deviation from the sample freezing point from 0° C. is proportional to the solute level in the sample fluid. This type of measuring device is sometimes referred to as a freezing point depression osmometer.

Presently, freezing point depression measurements are made ex vivo by removing tear samples from the eye using a micropipette or capillary tube, expelling the tear samples into a cup, and measuring the depression of the freezing point that results from heightened osmolarity. However, these ex vivo measurements are often plagued by many difficulties. For example, to perform freezing point depression analysis of the tear sample, a relatively large volume must be collected, typically on the order of 1-5 microliters (μL) of tear film. Because no more than about 10 to 100 nanoliters (nL) of tear sample can be obtained at any one time from a KCS patient, the collection of sufficient amounts of fluid for conventional ex vivo techniques requires a physician to induce reflex tearing in the patient. Reflex tearing is caused by a sharp or prolonged irritation to the ocular surface, akin to when a large piece of dirt becomes lodged in one's eye. Reflex tears are more dilute, i.e. have fewer solute ions than the tears that are normally found on the eye. Any dilution of the tear film invalidates the diagnostic ability of an osmolarity test for dry eye, and therefore make currently available ex vivo methods prohibitive in a clinical setting.

A similar ex vivo technique is vapor pressure osmometry, where a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature is raised to the dew point of the sample. The reduction in dew point proportional to water is then converted into osmolarity. Because of the induction of reflex tearing and the large volume requirements for existing vapor pressure osmometers, they are currently impractical for determination of dry eye.

The Clifton Nanoliter Osmometer, available from Clifton Technical Physics of Hartford, N.Y., USA, is a freezing point depression osmometer and has been used extensively in laboratory settings to quantify the solute concentrations of KCS patients, but the machine requires a significant amount of training to operate. It generally requires hour-long calibrations and a skilled technician in order to generate acceptable data. The Clifton Nanoliter Osmometer is also bulky and relatively expensive. These characteristics invalidate its use as a clinical osmometer.

In contrast to ex vivo techniques that measure osmolarity of tear samples removed from the ocular surface, an in vivo technique that attempted to measure osmolarity directly on the ocular surface used a flexible pair of electrodes that were placed directly underneath the eyelid of the patient. The electrodes were then plugged into an LCR meter to determine the conductivity of the fluid surrounding them. While it has long been known that conductivity is directly related to the ionic concentration, and hence osmolarity of solutions, placing the sensor under the eyelid for half a minute likely induced reflex tearing. Moreover, the electrodes are difficult to manufacture and pose increased health risks to the patient as compared to simply collecting tears with a capillary. Moreover, many DES patients exhibit a discontinuous tear lake, such that the curvature of the discontinuity would substantially alter the measured conductivity using an exposed probe, increasing user-to-user variability.

It should be apparent from the discussion above that current osmolarity measurement techniques are unavailable in a clinical setting and can't attain the volumes necessary for dry eye patients.

SUMMARY

A fluid collection device comprising a body comprising a capsule interface, and a capsule configured to interface with the body via the capsule interface and configured to hold a sample receiving chip. The sample receiving chip comprises a substrate that receives an aliquot volume of a sample fluid, wherein the substrate is operatively shaped to receive the aliquot volume of sample fluid through capillary action, and a sample region of the substrate, sized such that the volume of the sample fluid is sufficient to operatively cover a portion of the sample region, whereupon energy properties of the sample fluid can be transduced to produce a sample fluid reading.

In one aspect, the collection device can comprise an ergonomic shape and weight as well as a rotational feature that converts a gross rotation of the collection device into a fine linear translation of a tip of the sample receiving chip. This can be advantageous, for example, where the sample fluid is tears collected from the meniscus.

In another aspect, the sample receiving chip can be shaped so that is can soften entrance into the meniscus and is not as menacing as a conventional pipette.

In another aspect, the body can comprise visual and/or auditory indicators configured to indicate when the capsule is correctly interfaced with the body and/or when the sample fluid is being transduced.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

Exemplary embodiments are described for measuring the osmolarity of an aliquot volume of a sample fluid (e.g., tear film, sweat, blood, or other fluids). The exemplary embodiments are configured to be relatively fast, non-invasive, inexpensive, and easy to use, with minimal risk of injury to the patient. Accurate measurements can be provided with as little as nanoliter volumes of a sample fluid. For example, a measuring device configured in accordance with the embodiments described herein can enable osmolarity measurement with no more than 20 μL of sample fluid, and typically much smaller volumes can be successfully measured. In one embodiment described further below, osmolarity measurement accuracy is not compromised by variations in the volume of sample fluid collected, so that osmolarity measurement is substantially independent of collected volume. The sample fluid can include tear film, sweat, blood, urine or other bodily fluids. It should be noted, however, that sample fluid can comprise other fluids, such as milk or other beverages.

Figure 1:
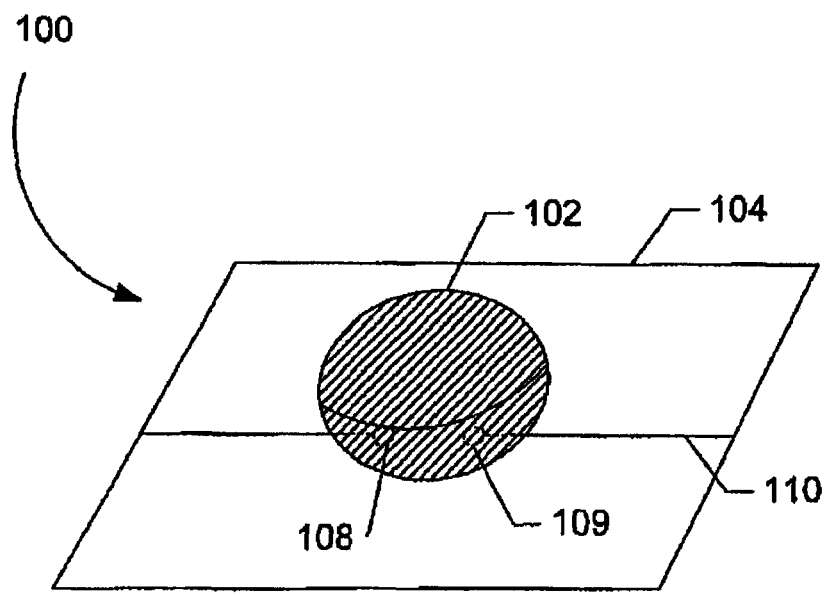
FIG. 1 illustrates an aliquot-sized sample receiving chip for measuring the osmolarity of a sample fluid in accordance with one embodiment.

FIG. 1 illustrates an exemplary embodiment of an osmolarity chip 100 that can be used to measure the osmolarity of a sample fluid 102, such as a tear film sample. In the example of FIG. 1, the chip 100 includes a substrate 104 with a sample region having sensor electrodes 108 and 109 and circuit connections 110 imprinted on the substrate. The electrodes 108 and 109 and circuit connections 110 are preferably printed using well-known photolithographic techniques. For example, current techniques enable the electrodes 108 and 109 to have a diameter in the range of approximately one (1) to eighty (80) microns, and spaced apart sufficiently so that no conductive path exists in the absence of sample fluid. Currently available techniques, however, can provide electrodes of less than one micron in diameter, and these are sufficient for a chip constructed in accordance with the embodiments described herein.

The amount of sample fluid needed for measurement is no more than is necessary to extend from one electrode to the other, thereby providing an operative conductive path. The photolithographic scale of the chip 100 permits the measurement to be made for aliquot-sized samples in a micro- or nano-scale level. For example, reliable osmolarity measurement can be obtained with a sample volume of less than 20 µL of tear film. A typical sample volume can be less than one hundred nanoliters (100 nL). It is expected that it will be relatively easy to collect 10 nL of a tear film sample even from patients suffering from dry eye.

The chip 100 can be configured to transfer energy to the sample fluid 102 and enable detection of the sample fluid energy properties. In this regard, a current source can be applied across the electrodes 108 and 109 through the connections 110. The osmolarity of the sample fluid can be measured by sensing the energy transfer properties of the sample fluid 102. The energy transfer properties can include, for example, electrical conductivity, such that the impedance of the sample fluid is measured, given a particular amount of electrical power, e.g., current, that is transferred into the sample through the connections 110 and the electrodes 108 and 109.

If conductivity of the sample fluid is to be measured, then preferably a sinusoidal signal on the order of ten volts at approximately 10 kHz is applied. The real and imaginary parts of the complex impedance of the circuit path from one electrode 108 through the sample fluid 102 to the other electrode 109 are measured. At the frequencies of interest, it is likely that the majority of the electrical signal will be in the real half of the complex plane, which reduces to the conductivity of the sample fluid. This electrical signal (hereafter referred to as conductivity) can be directly related to the ion concentration of the sample fluid 102, and the osmolarity can be determined. Moreover, if the ion concentration of the sample fluid 102 changes, the electrical conductivity and the osmolarity of the fluid will change in a corresponding manner. Therefore, the osmolarity can be reliably obtained. In addition, because the impedance value does not depend on the volume of the sample fluid 102, the osmolarity measurement can be made substantially independent of the sample volume.

As an alternative to the input signal described above, more complex signals can be applied to the sample fluid the response of which will contribute to a more thorough estimate of osmolarity. For example, calibration can be achieved by measuring impedances over a range of frequencies. These impedances can be either simultaneously, via combined waveform input and Fourier decomposition, or sequentially measured. The frequency versus impedance data will provide information about the sample and the relative performance of the sample fluid measurement circuit.

Figure 2:
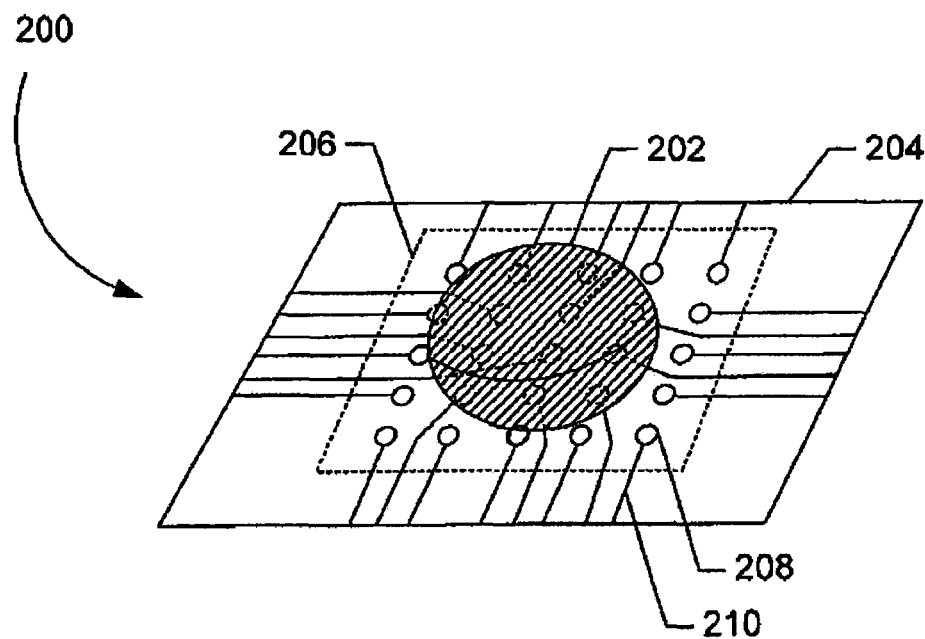
FIG. 2 illustrates an alternative embodiment of a sample receiving chip that includes a circuit region with an array of electrodes imprinted with photolithography techniques.

FIG. 2 illustrates an alternative embodiment of a sample receiving chip 200 that can be configured to measure osmolarity of a sample fluid 202, wherein the chip comprises a substrate layer 204 with a sample region 206 comprising an imprinted circuit that includes an array of electrodes 208. In the illustrated embodiment of FIG. 2, the sample region 206 has a 5-by-5 array of electrodes that are imprinted with photolithographic techniques, with each electrode 208 having a connection 210 to one side of the substrate 204. Not all of the electrodes 208 in FIG. 2 are shown with a connection, for simplicity of illustration. The electrode can provide measurements to a separate processing unit, described further below.

The electrode array of FIG. 2 can provide a means to measure the size of the tear droplet 202 by detecting the extent of conducting electrodes 208 to thereby determine the extent of the droplet. In particular, processing circuitry can determine the number of electrodes that are conducting, and therefore the number of adjacent electrodes that are covered by the droplet 202 can be determined. The planar area of the substrate that is covered by the sample fluid can thereby be determined. With a known nominal surface tension of the sample fluid, the height of the sample fluid volume over the planar area can also be reliably estimated, and therefore the volume of the droplet 202 can be determined.

Figure 3:
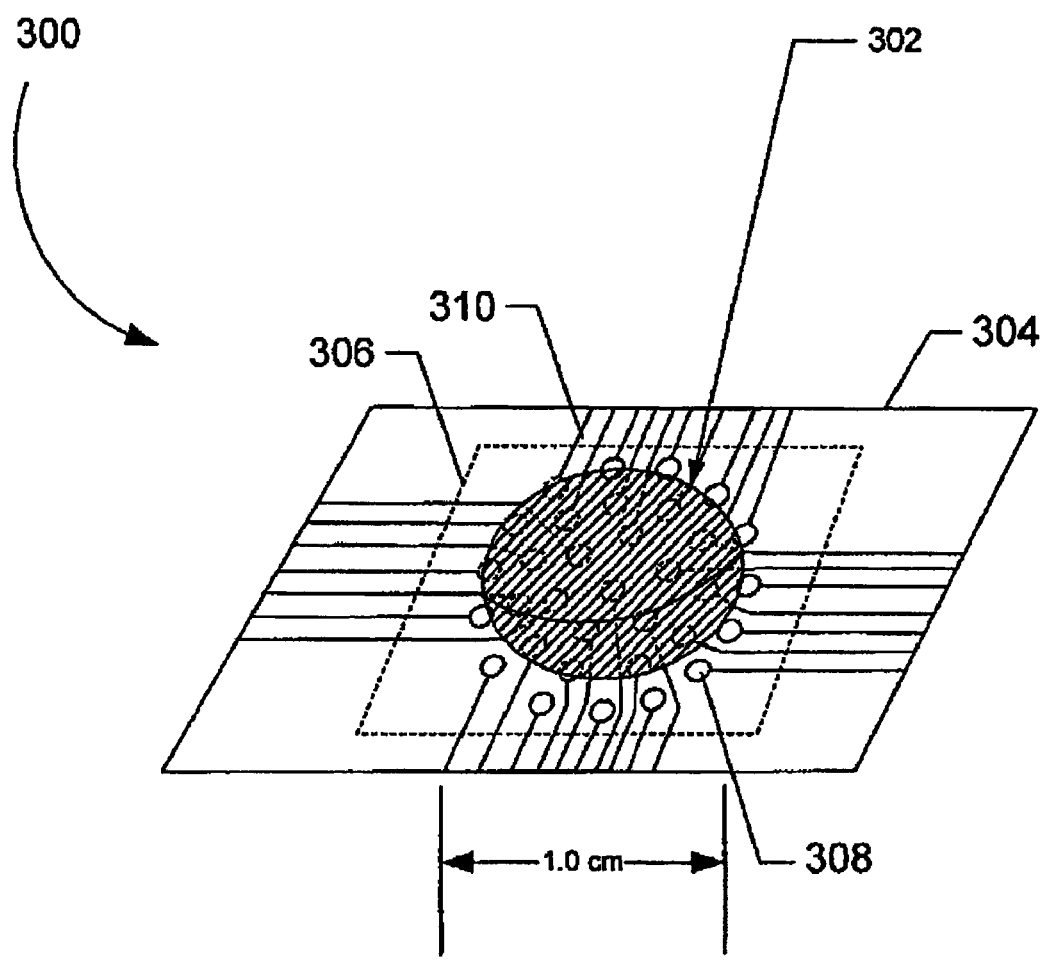
FIG. 3 illustrates another alternative embodiment of the FIG. 1 chip, wherein a circuit region includes printed electrodes arranged in a plurality of concentric circles.

FIG. 3 illustrates another alternative embodiment of a sample receiving chip 300 on which a sample fluid 302 is deposited. The chip comprises a substrate layer 304, wherein a sample region 306 is provided with electrodes 308 that are configured in a plurality of concentric circles. In a manner similar to the square array of FIG. 2, the circular arrangement of the FIG. 3 electrodes 308 can also provide an estimate of the size of the sample fluid volume 302 because the droplet typically covers a circular or oval area of the sample region 302. Processing circuitry can be configured to detect the largest (outermost) circle of electrodes that are conducting, and thereby determine a planar area of coverage by the fluid sample. As before, the determined planar area can provide a volume estimate, in conjunction with a known surface tension and corresponding volume height of the sample fluid 302. In the example of FIG. 3, the electrodes 308 can be printed using well-known photolithography techniques that currently permit electrodes to have a diameter in the range of one (1) to eighty (80) microns. This allows the sub-microliter droplet to substantially cover the electrodes. The electrodes can be printed over an area sized to receive the sample fluid, generally covering 1 mm$^2$ to 1 cm$^2$.

The electrodes and connections shown in FIG. 1, FIG. 2, and FIG. 3 can be imprinted on the respective substrate layers as electrodes with contact pads, using photolithographic techniques. For example, the electrodes can be formed with different conductive metallization such as aluminum, platinum, titanium, titanium-tungsten, and other similar material. In one embodiment, the electrodes can be formed with a dielectric rim to protect field densities at the edges of the electrodes. This can reduce an otherwise unstable electric field at the rim of the electrode.

Figure 4:
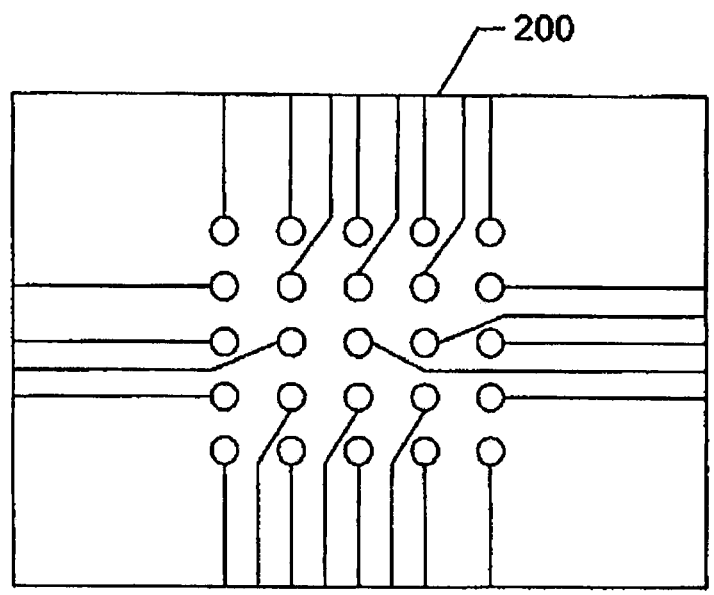
FIG. 4 is a top view of the chip shown in FIG. 2.
Figure 5:
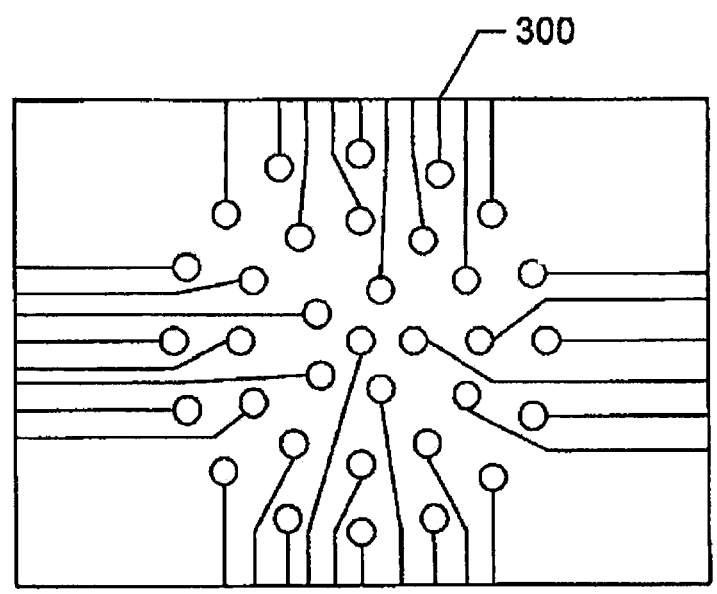
FIG. 5 is a top view of the chip shown in FIG. 3.

Top views of the exemplary embodiments of the chips 200 and 300 are illustrated in FIG. 4 and FIG. 5, respectively. The embodiments show the detailed layout of the electrodes and the connections, and illustrate how each electrode can be electrically connected for measuring the electrical properties of a sample droplet. As mentioned above, the layout of the electrodes and the connections can be imprinted on the substrate 100, 200, 300 using well-known photolithographic techniques.

Figure 6:
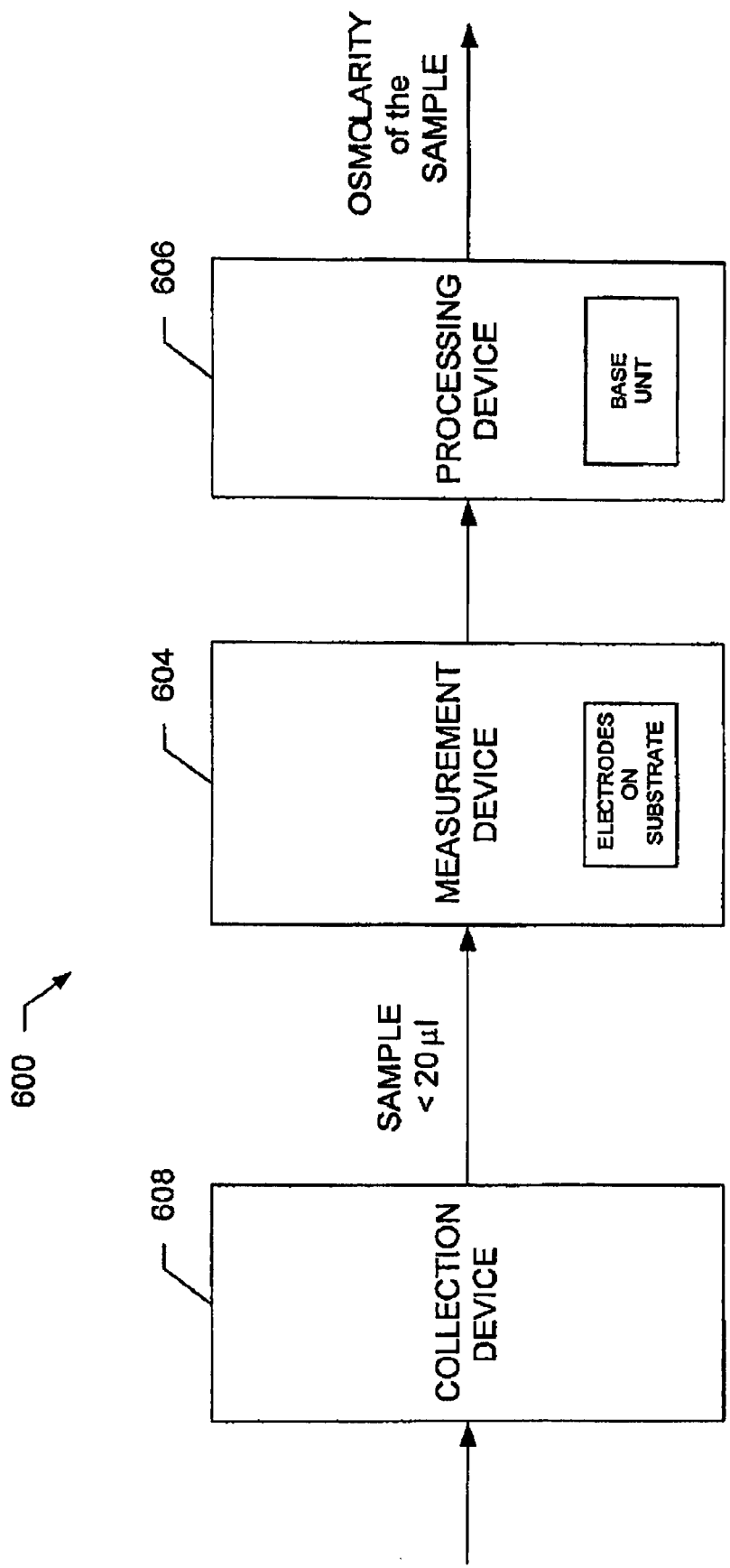
FIG. 6 is a block diagram of an osmolarity measurement system configured in accordance with one embodiment.

FIG. 6 is a block diagram of an osmometry system 600, configured in accordance with an embodiment, showing how information is determined and used in a process that determines osmolarity of a sample fluid. The osmometry system 600 can include a measurement device 604 and a processing device 606. The measurement device can receive a volume of sample fluid from a collection device 608. The collection device 608 can comprise, for example, a micropipette or capillary tube. The collection device 608 can be configured to collect a sample tear film of a patient, such as by using negative pressure from a fixed-volume micropipette or charge attraction from a capillary tube to draw a small tear volume from the vicinity of the ocular surface of a patient.

The measurement device 604 can comprise a system that transfers energy to the fluid in the sample region and detects the imparted energy. For example, the measurement device 604 can comprise circuitry that provides electrical energy in a specified waveform, such as from a function generator, to the electrical path comprising two electrodes bridged by the sample fluid. The processing device 606 can be configured to detect the energy imparted to the sample fluid and determine osmolarity. The processing device can comprise, for example, a system including an RLC multimeter that produces data relating to the reactance of the fluid that forms the conductive path between two electrodes, and including a processor that determines osmolarity through a table look-up scheme. If desired, the processing device can be housed in a base unit that receives one of the chips described above.

As mentioned above, a sample sufficient to provide an osmolarity measurement can contain less than 20 microliters (μL) of fluid. A typical sample of tear film can be collected by a fluid collector such as a capillary tube, which often contains less than one microliter of tear film. Medical professionals will be familiar with the use of micropipettes and capillary tubes, and will be able to easily collect the small sample volumes described herein, even in the case of dry eye sufferers.

The collected sample fluid can be expelled from the collection device 608 to the measurement device 604. The collection device can be positioned above the sample region of the chip substrate either manually by a medical professional or by being mechanically guided over the sample region. In one embodiment, for example, the collection device, e.g., a capillary tube, is mechanically guided into position with an injection-molded plastic hole in a base unit, or is fitted to a set of clamps with precision screws, e.g., a micromanipulator with needles for microchip interfaces. In another embodiment, the guide is a computer-guided feedback control circuitry that holds the capillary tube and automatically lowers it into the proper position.

The electrodes and connections of the chips measure energy properties of the sample fluid, such as conductivity, and enable the measured properties to be received by the processing device 606. The measured energy properties of the sample fluid include electrical conductivity and can also include other parameters, such as both parts of the complex impedance of the sample, the variance of the noise in the output signal, and the measurement drift due to resistive heating of the sample fluid. The measured energy properties are processed in the processing device 606 to provide the osmolarity of the sample. In one embodiment, the processing device 606 comprises a base unit that can accept a chip and can provide electrical connection between the chip and the processing device 606. In another embodiment, the base unit can include a display unit for displaying osmolarity values. It should be noted that the processing device 606 and, in particular, the base unit can be a hand-held unit.

Figure 7:
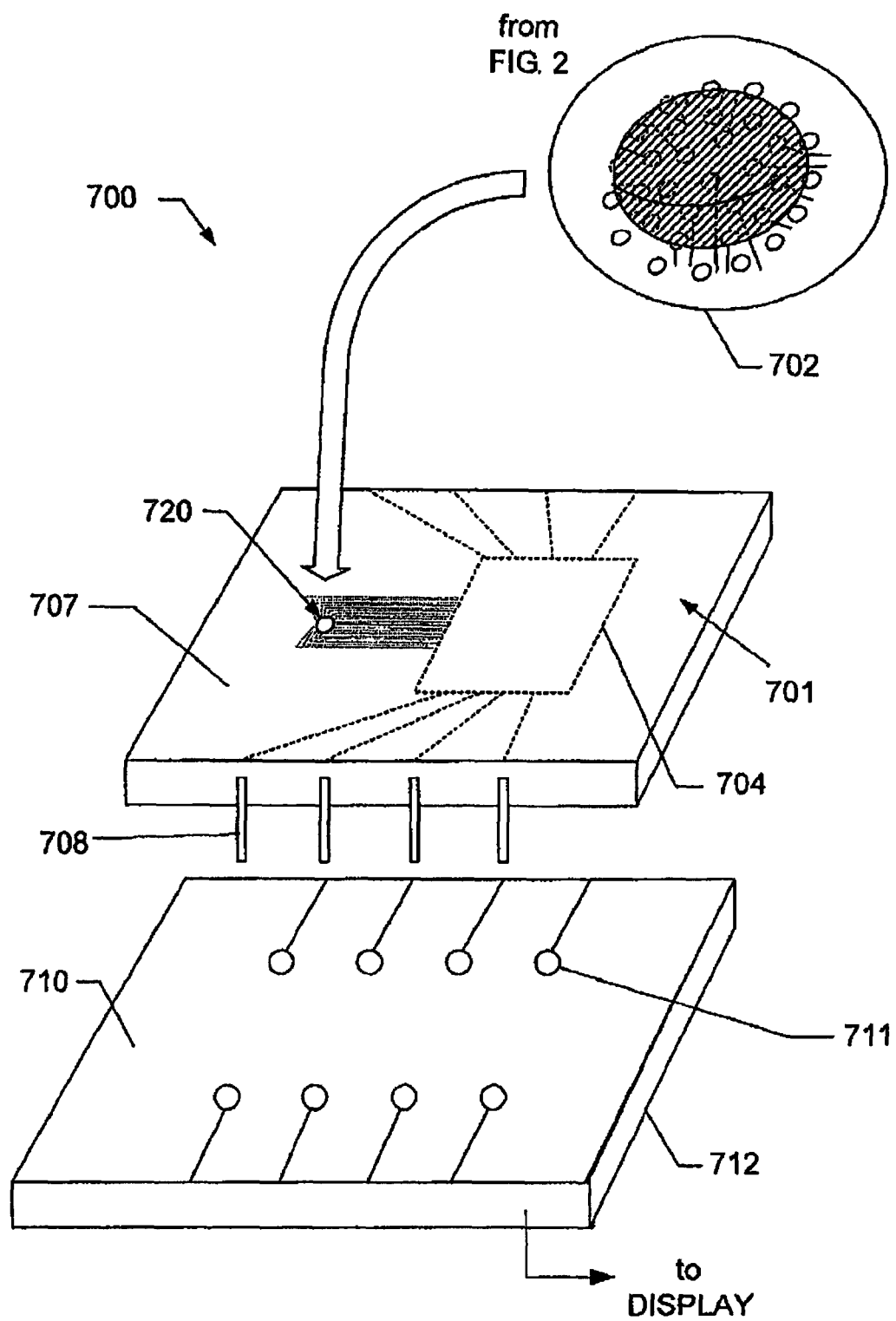
FIG. 7 is a perspective view of a tear film osmolarity measurement system constructed in accordance with one embodiment.

FIG. 7 is a perspective view of a tear film osmolarity measuring system 700 constructed in accordance with one embodiment. In the illustrated embodiment of FIG. 7, the exemplary system 700 includes a measuring unit 701 that comprises a chip, such as one of the chips described above, and a connector or socket base 710, which provides the appropriate measurement output. The system 700 can be configured to determine osmolarity by measuring electrical conductivity of the sample fluid. Therefore, the measurement chip 701 can comprise an integrated circuit (IC) chip with a substrate having a construction similar to that of the chips described above in connection with FIG. 1 through FIG. 5. Thus, the chip 701 can include a substrate layer with a sample region that is defined by at least two electrodes printed onto the substrate layer. It will be understood that such details are of a scale too small to be visible in FIG. 7, but see FIG. 1 through FIG. 5, examples of these details. The substrate and sample region can be encased within an inert package, in a manner that will be known to those skilled in the art. In particular, the chip 701 can be fabricated using conventional semiconductor fabrication techniques into an IC package 707 that includes electrical connection legs 708 that permit electrical signals to be received by the chip 701 and output to be communicated outside of the chip. The packaging 707 can provide a casing that makes handling of the chip more convenient and helps reduce evaporation of the sample fluid.

Figure 8:
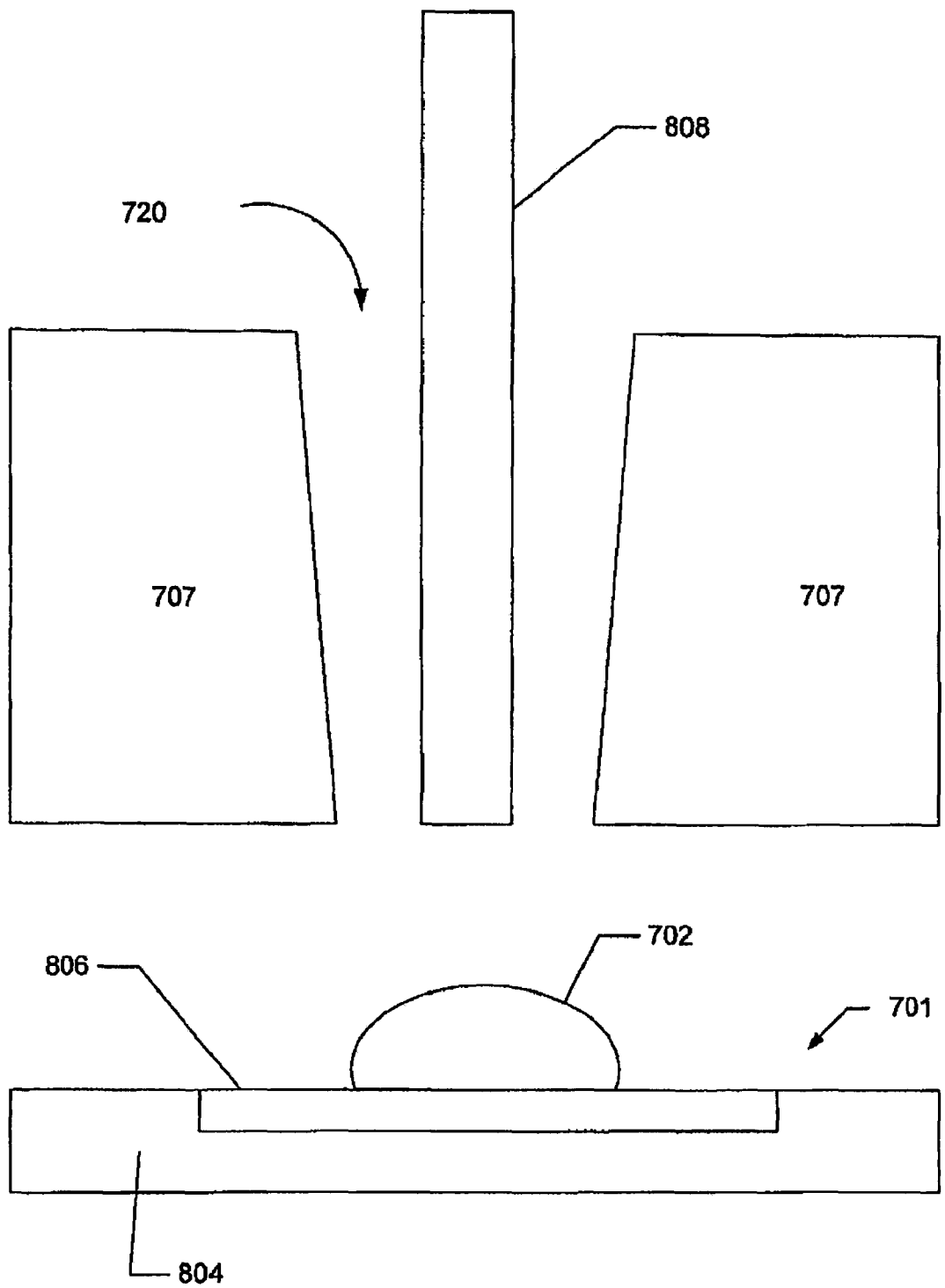
FIG. 8 is a side section of the sample receiving chip showing the opening in the exterior packaging in accordance with one embodiment.

FIG. 8 shows that the measurement chip 701 can be fabricated with an exterior opening hole 720 into which the sample fluid 702 can be inserted. Thus, the hole 720 can be formed in the semiconductor packaging 707 to provide a path through the chip exterior to the substrate 804 and the sample region 806. The collection device, such as a micropipette or capillary tube, 808 can be positioned into the hole 720 such that the sample fluid 702 is expelled from the collection device directly onto the sample region 806 of the substrate 804. The hole 720 can be sized to receive the tip of the collection device. The hole 720 forms an opening or funnel that leads from the exterior of the chip onto the sample region 806 of the substrate 804. In this way, the sample fluid 702 can be expelled from the collection device 808 and can be deposited directly on the sample region 806 of the substrate 804. The sample region can be sized to receive the volume of sample fluid from the collection device. In FIG. 8, for example, the electrodes can form a sample region 806 that is generally in a range of approximately 1 mm$^2$ to 1 cm$^2$ in area.

Returning to FIG. 7, the chip 701 can include processing circuitry 704 that comprises, for example, a function generator that generates a signal of a desired waveform, which can be applied to the sample region electrodes of the chip, and a voltage measuring device to measure the root-mean-square (RMS) voltage value that is read from the chip electrodes. The function generator can be configured to produce high frequency alternating current (AC) to avoid undesirable direct current (DC) effects for the measurement process. The voltage measuring device can incorporate the functionality of an RLC measuring device. Thus, the chip 701 can incorporate the measurement circuitry as well as the sample region electrodes. The processing circuitry can include a central processing unit (CPU) and associated memory that can store programming instructions (such as firmware) and also can store data. In this way, a single chip can include the electrodes and associated connections for the sample region, and on a separate region of the chip, can also include the measurement circuitry. This configuration can minimize the associated stray resistances of the circuit structures.

As noted above, the processing circuitry 704 can be configured to apply a signal waveform to the sample region electrodes. The processing circuitry can also receive the energy property signals from the electrodes and determine the osmolarity value of the sample fluid. For example, the processing unit can receive electrical conductivity values from a set of electrode pairs. Those skilled in the art will be familiar with techniques and circuitry for determining the conductivity of a sample fluid that forms a conducting path between two or more electrodes.

Figure 9:
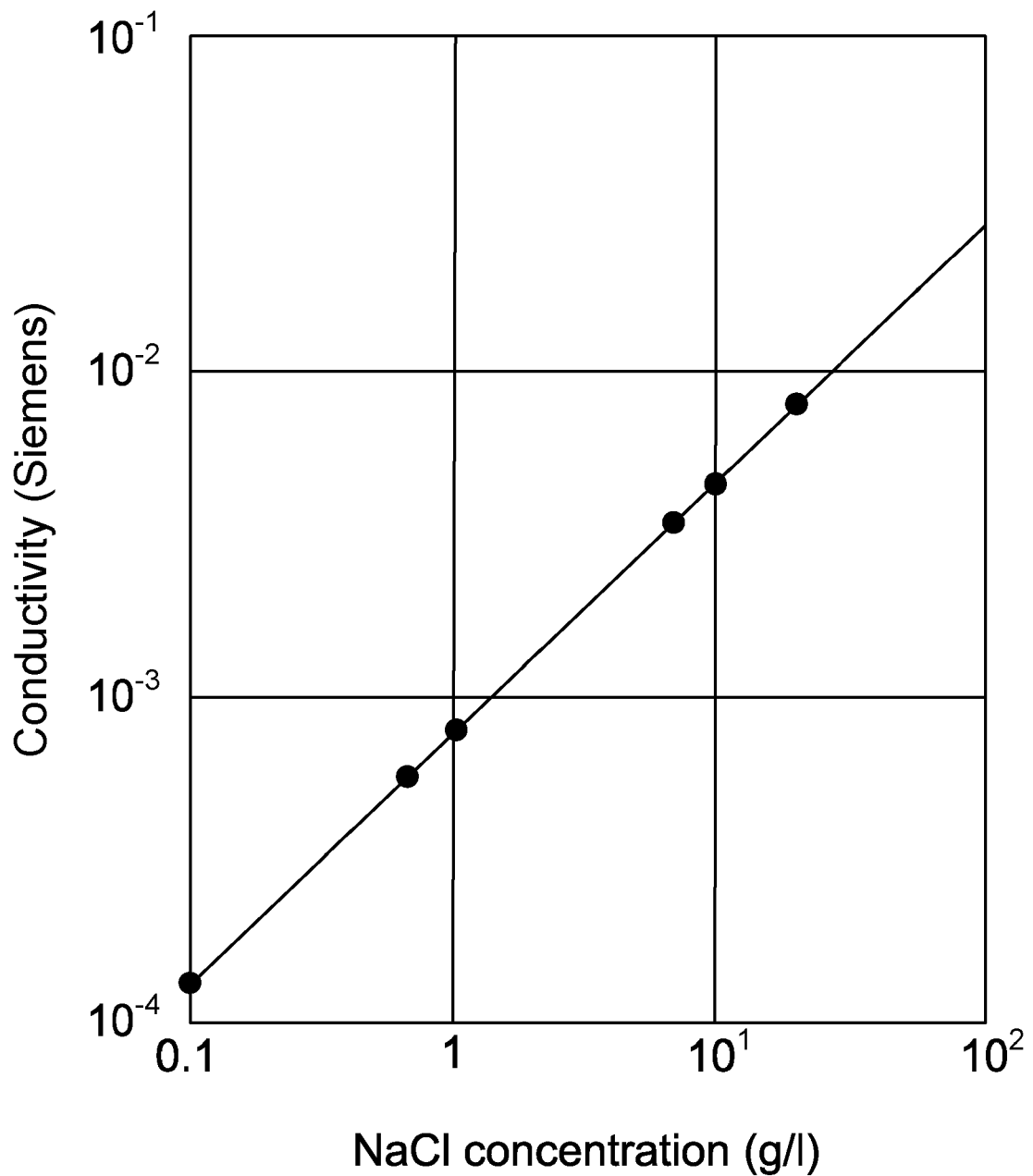
FIG. 9 is a calibration curve relating the sodium content of the sample fluid with electrical conductivity.

In the example of FIG. 7, the processing unit 704 can be configured to produce signal waveforms at a single frequency, such as 100 kHz and 10 Volts peak-to-peak. The processing circuitry 704 can then determine the osmolarity value from the sodium content correlated to the electrical conductivity using a calibration curve, such as the curve shown in FIG. 9. In this case, the calibration curve can be constructed as a transfer function between the electrical conductivity (voltage) and the osmolarity value, i.e., the sodium content. It should be noted, however, that other calibration curves can also be constructed to provide transfer functions between other energy properties and the osmolarity value. For example, the variance, autocorrelation and drift of the signal can be included in an osmolarity calculation. If desired, the osmolarity value can also be built upon multi-variable correlation coefficient charts or neural network interpretation so that the osmolarity value can be optimized with an arbitrarily large set of measured variables.

In an alternative to the embodiment shown in FIG. 7, the processing unit 704 can be configured to produce signal waveforms of a predetermined frequency sweep, such as 1 kHz to 100 kHz in 1 kHz increments, and store the conductivity and variance values received from the set of electrode pairs at each frequency. The output signal versus frequency curve can then be used to provide higher order information about the sample, which can be used with the aforementioned transfer functions to produce an ideal osmolarity reading.

As shown in FIG. 7, the base socket connector 710 can receive the pins 708 of the chip 701 into corresponding sockets 711. The connector 710, for example, can supply the requisite electrical power to the processing circuitry 704 and electrodes of the chip. Thus, the chip 701 can include the sample region electrodes and the signal generator and processing circuitry necessary for determining osmolarity and the output comprising the osmolarity value can be communicated off the chip via the pins 708 through the connector 710 and to display readout.

If desired, the base connector socket 710 can include a Peltier layer 712 located beneath the sockets that receive the pins 708 of the chip 701. Those skilled in the art will understand that a Peltier layer comprises an electrical/ceramic junction such that properly applied current can cool or heat the Peltier layer. In this way, the sample chip 701 can be heated or cooled, thereby further controlling evaporation of the sample fluid. It should be apparent that evaporation of the sample fluid should be carefully controlled, to ensure accurate osmolarity values obtained from the sample fluid.

Figure 10:
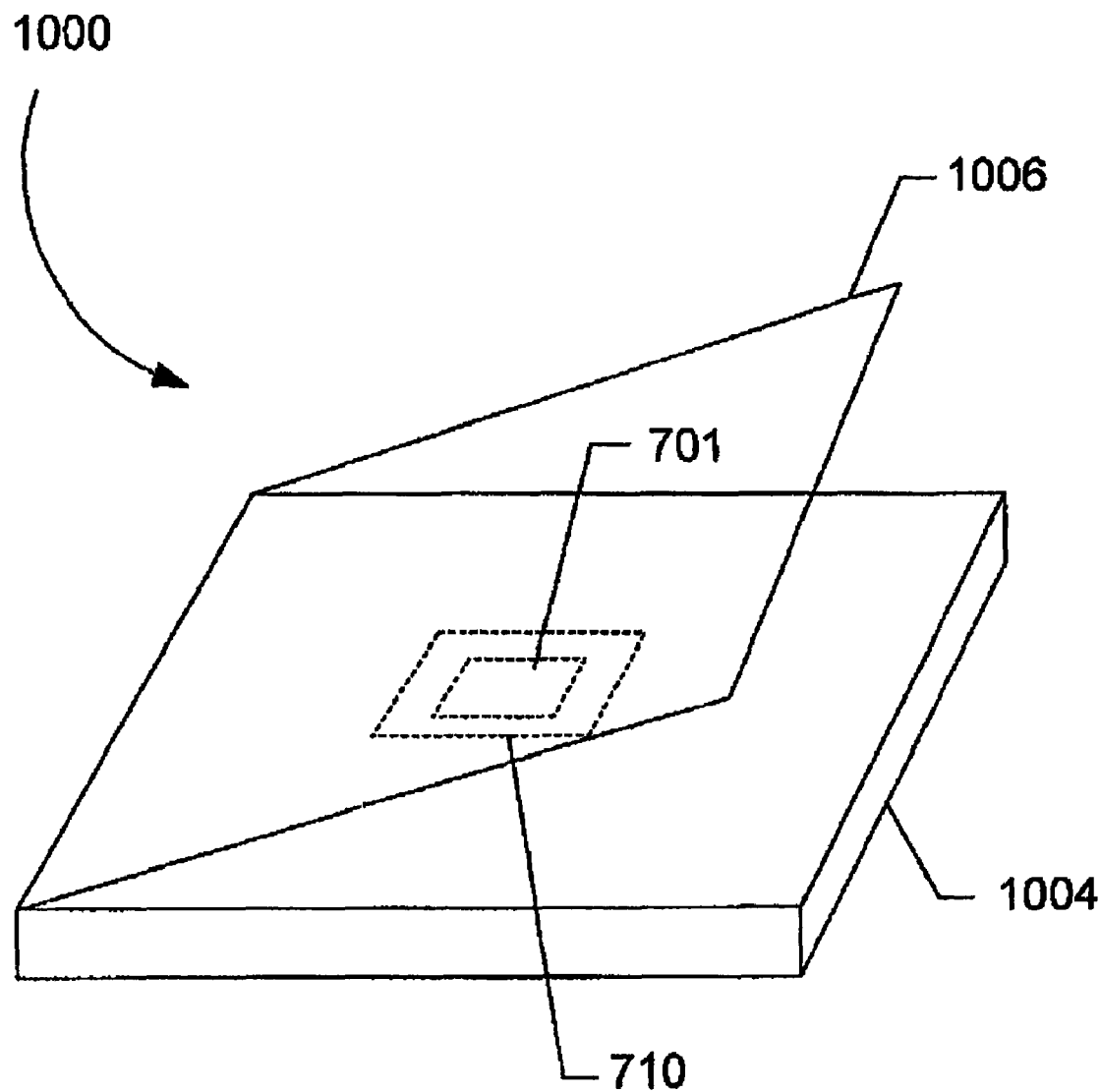
FIG. 10 illustrates a hinged base unit of the osmometer that utilizes the sample receiving chips described in FIGS. 1-5.

FIG. 10 shows an alternative embodiment of an osmometer in which the chip does not include an on-chip processing unit such as described above, but rather includes limited circuitry comprising primarily the sample region electrodes and interconnections. That is, the processing unit is separately located from the chip and can be provided in, e.g., the base unit.

FIG. 10 shows in detail an osmometer 1000 that includes a base unit 1004, which houses the base connector 710, and a hinged cover 1006 that closes over the base connector 710 and a received measurement chip 701. Thus, after the sample fluid has been dispensed on the chip, the chip can be inserted into the socket connector 710 of the base unit 1004 and the hinged cover 1006 can be closed over the chip to reduce the rate of evaporation of the sample fluid.

It should be noted that the problem with relatively fast evaporation of the sample fluid can generally be handled in one of two ways. One way is to measure the sample fluid voltage quickly and as soon possible after the droplet is placed on the sample region of the chip. Another way is to enable the measuring unit to measure the rate of evaporation along with the corresponding changes in conductivity values. The processing unit can then post-process the output to estimate the osmolarity value. The processing can be performed in the hardware and/or in software stored in the hardware. Thus, the processing unit can incorporate different processing techniques such as using neural networks to collect and learn about characteristics of the fluid samples being measured for osmolarity, as well as temperature variations, volume changes, and other related parameters so that the system can be trained in accordance with neural network techniques to make faster and more accurate osmolarity measurements.

Figure 11:
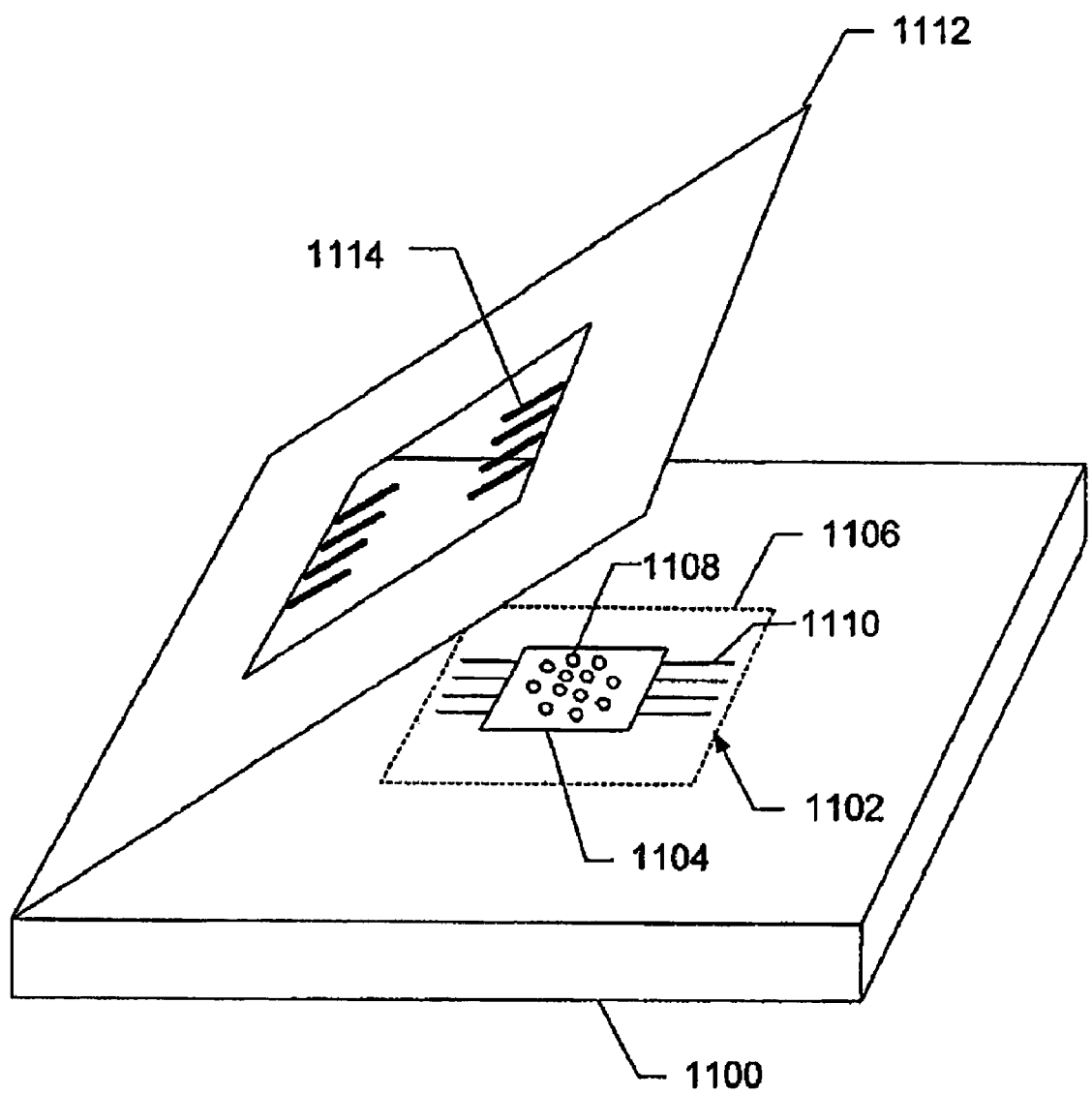
FIG. 11 illustrates a probe card configuration for the sample receiving chip and processing unit.

FIG. 11 shows another alternative construction, in which the osmolarity system uses a sample receiving chip 1102 that does not include IC packaging such as shown in FIG. 7. Rather, the FIG. 11 measurement chip 1102 is configured as a chip with an exposed sample region comprising the electrodes and associated connections, but the processing circuitry is located in the base unit for measuring the energy properties of the sample fluid. In this alternative construction, a connector similar to the connector socket 710 can allow transmission of measured energy properties to the processing unit in the base unit. Those skilled in the art will understand that such a configuration is commonly referred to a probe card structure.

FIG. 11 shows a probe card base unit 1100 that can receive a sample chip probe card 1102 that comprises a substrate 1104 with a sample region 1106 on which are formed electrodes 1108 that can be wire bonded to edge connectors 1110 of the probe card. When the hinged lid 1112 of the base unit is closed down over the probe card, connecting tines 1114 on the underside of the lid can be configured to come into mating contact with the edge connectors 1110. In this way, the electrodes of the sample region 1106 can be coupled to the processing circuitry and measurement can take place. The processing circuitry of the probe card embodiment of FIG. 11 can, e.g., be configured in either of the configurations described above. That is, the processing to apply current to the electrodes and to detect energy properties of the sample fluid and determine osmolarity can be located on-chip, on the substrate of the probe card 1102, or the processing circuitry can be located off-chip, in the base unit 1100.

In all the alternative embodiments described above, the osmometer a new measurement chip can be placed into the base unit while the hinged top is open. Upon placement into the base unit, the chip can be powered up and begin monitoring its environment. Recording output signals from the chip at a rate of, for example, 1 kHz, should fully capture the behavior of the system. Placing a sample onto any portion of the electrode array should generate high signal-to-noise increase in conductivity between any pair of electrodes covered by the sample fluid. The processing unit can then recognize the change in conductivity as being directly related to the addition of sample fluid, and can begin conversion of electronic signals into osmolarity data once this type of change is identified. This strategy can occur without intervention by medical professionals. That is, the chip processing can be initiated upon coupling to the base unit and is not necessarily dependent on operating the lid of the base unit or any other user intervention.

In any of the configurations described above, either the "smart chip" with processing circuitry on-chip (FIG. 7), or the electrode-only configuration with processing circuitry off-chip (FIG. 10), in a packaged chip (FIG. 7 and FIG. 10) or in a probe card (FIG. 11), the sample receiving chip can be disposed of after each use, so that the base unit serves as a platform for interfacing with the disposable measurement chip. As noted, the base unit can also include relevant control, communication, and display circuits (not shown), as well as software, or such features can be provided off-chip in the base unit or elsewhere. In this regard, the processing circuitry can be configured to automatically provide sufficient power to the sample region electrodes to irreversibly oxidize them after a measurement cycle, such that the electrodes are rendered inoperable for any subsequent measurement cycle. Upon inserted a used chip into the base unit, the user will be given an indication that the electrodes are inoperable. This helps prevent inadvertent multiple use of a sample chip, which can lead to inaccurate osmolarity readings and potentially unsanitary conditions.

A secondary approach to ensure that a previously used chip is not placed back into the machine includes encoding serial numbers, or codes directly onto the chip. The base unit will store the used chip numbers in memory and cross-reference them against new chips placed in the base connector. If the base unit finds that the serial number of the used chip is the same as an old chip, then the system will refuse to measure osmolarity until a new chip is inserted. It is important to ensure use of a new chip for each test because proteins adsorb and salt crystals form on the electrodes after evaporation has run its course, which corrupt the integrity of the measuring electrodes.

Figure 12:
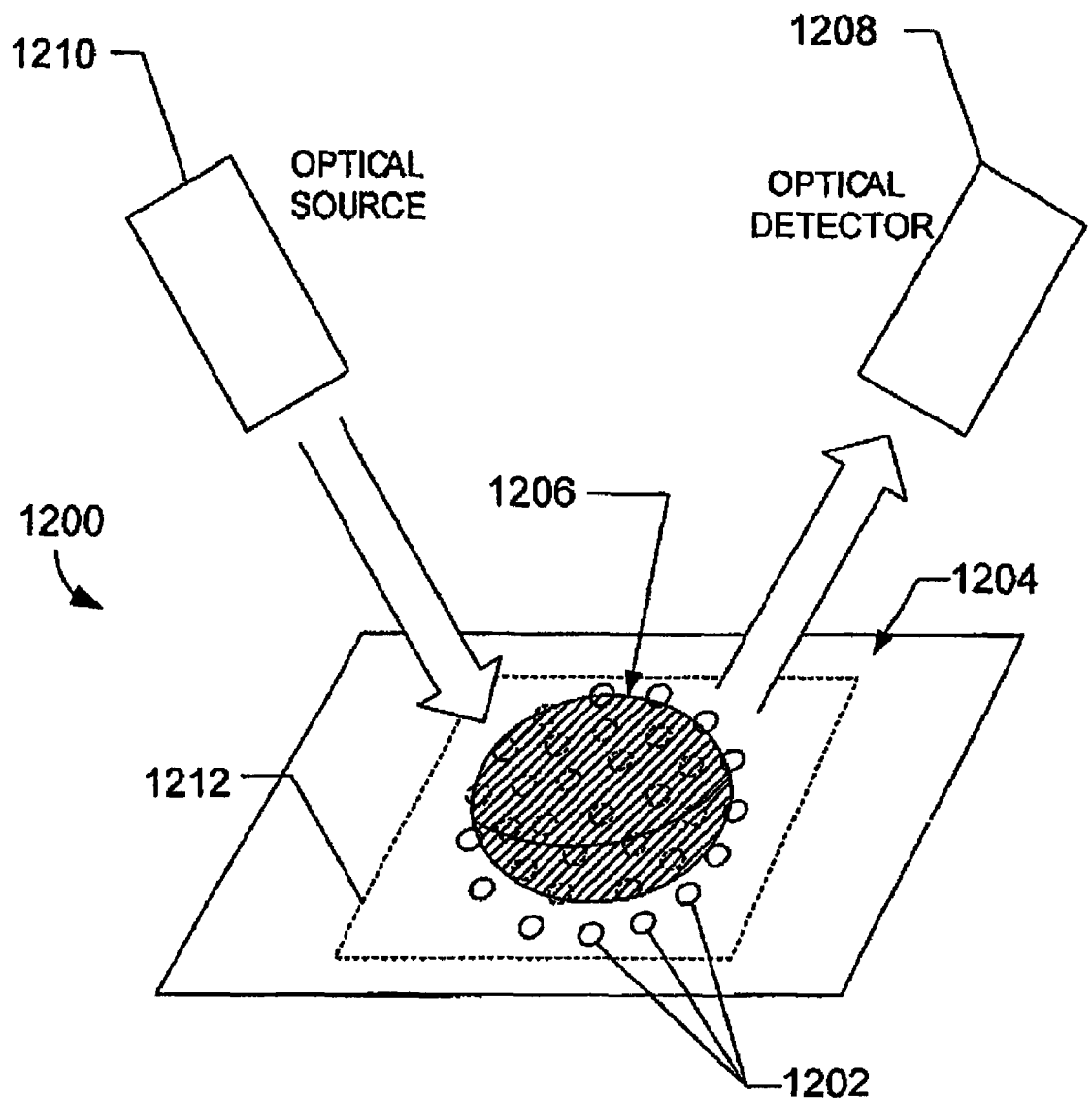
FIG. 12 illustrates an optical osmolarity measurement system constructed in accordance with one embodiment.

In a further embodiment shown, in FIG. 12, the osmolarity of a sample fluid can be measured optically in an optical measurement system 1200 by using optical indicators 1202 disposed on a measuring region 1212 of the chip substrate 1204. The optical indicators 1202 can comprise, for example, nano-scale spheres, also called nanobeads that are coated with chemicals whose luminescence varies with exposure to sample fluid of varying osmolarity, i.e. ionophores, or plasmon resonances. The nanobeads 1202 can be deposited on the chip substrate 1204 on top of the electrodes described above for the conductivity-measuring chips. The electrodes can be useful, e.g., for determining the volume of the sample fluid, as described above. However, other volume-measuring elements can be used to determine the volume of the sample fluid. Preferably, but not necessarily, the optical chip is produced with inert packaging such as described above in connection with FIG. 7, including a chip opening hole through which the collection device tip can be inserted. The sample fluid can then be expelled from the collection device and the sample fluid can come into contact with a predetermined, fixed number of the nanobeads per electrode site, which become immersed in the sample fluid.

When the nanobeads 1202 are illuminated with an optical energy source 1210, such as a laser, the beads 1202 will fluoresce in accordance with the osmolarity of the sample fluid 1206. The fluorescence can be detected using a suitable optical detector light receiving device 1208, such as a conventional charge-coupled device (CCD) array, photodiode, or the like. The resulting output signal of the light receiving array can indicate the osmolarity value of the sample fluid. It should be noted that the nano-scale beads are sized such that an aliquot-sized fluid sample 1206, i.e., no more than 20 microliters of the fluid, will ordinarily produce sufficient fluorescence to provide an output signal that can be detected by the light receiving device 1208 and that can indicate osmolarity of the sample fluid. The amount of fluorescence can be normalized by calculating how many nanobeads were activated by fluid and by measuring which electrode pairs were activated by the sample fluid. This normalization accounts for the sample volume and allows the volume independence feature of the prior embodiment to be retained.

Figure 13:
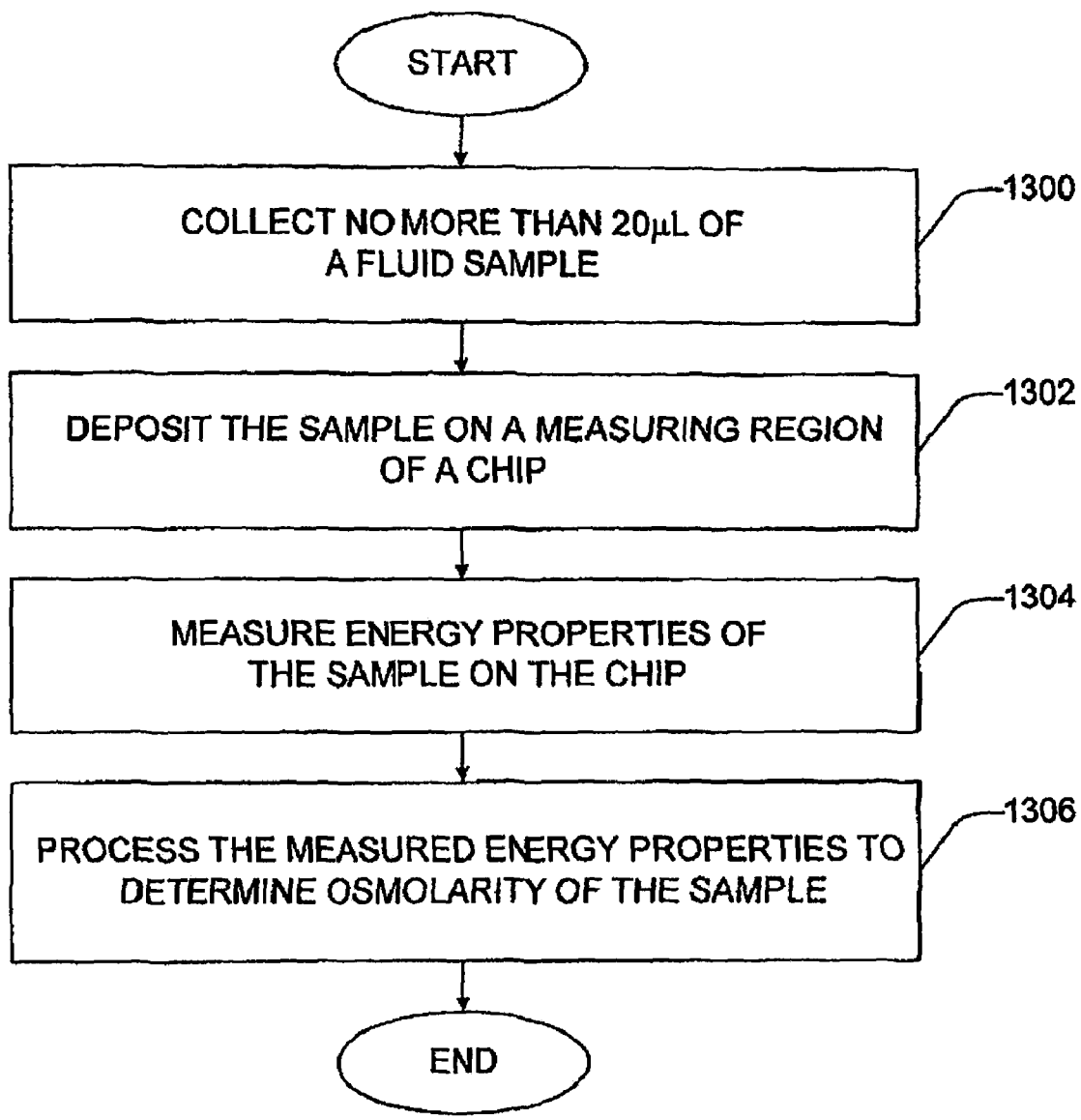
FIG. 13 is a flowchart describing an exemplary osmolarity measurement technique in accordance with one embodiment.

FIG. 13 is a flowchart describing an exemplary osmolarity measurement technique in accordance with one embodiment. First, a body fluid sample, such as a tear film, is collected in step 1300. The sample typically, e.g., contains less than one microliter. At step 1302, the collected sample can be deposited on a sample region of a chip substrate. The energy properties of the sample can then be measured at step 1304. The measured energy properties can then be processed, at step 1306, to determine the osmolarity of the sample. If the chip operates in accordance with electrical conductivity measurement, then the measurement processing at step 1306 can include the "electrode oxidation" operation described above that renders the chip electrodes inoperable for any subsequent measuring cycles.

In the measurement process for a conductivity measuring system, a substantially instantaneous shift is observed from the open circuit voltage to a value that closely represents the state of the sample at the time of collection, upon placement of a sample tear film on an electrode array of the substrate. Subsequently, a drift in the conductivity of the sample will be reflected as a continual change in the output.

The output of the measurement chip can be a time-varying voltage that is translated into an osmolarity value. Thus, in a conductivity-based system, more information than just the "electrical conductivity" of the sample can be obtained by measuring the frequency response over a wide range of input signals, which improves the end stage processing. For example, the calibration can be made over a multiple frequencies, e.g., measure ratio of signals at 10, 20, 30, 40, 50, 100 Hz, etc. to make the measurement process a relative calculation. This makes the chip-to-chip voltage drift small. The standard method for macroscale electrode based measurements, i.e., in a pH meter, or microcapillary technique, is to rely upon known buffers to set up a linear calibration curve. Because photolithography is an extremely reproducible manufacturing technique, when coupled to a frequency sweep, calibration can be performed without operator intervention.

As mentioned above, the processing of the energy properties can be performed in a neural network configuration, where the seemingly disparate measured data points obtained from the energy properties can be used to provide more accurate osmolarity reading than from a single energy property measurement. For example, if only the electrical conductivity of the sample is measured, then the calibration curve can be used to simply obtain the osmolarity value corresponding to the conductivity. This osmolarity value, however, generally will not be as accurate as the output of the neural network.

The neural network can be designed to operate on a collection of calibration curves that reflects a substantially optimized transfer function between the energy properties of the sample fluid and the osmolarity. Thus, in one embodiment, the neural network can be configured to construct a collection of calibration curves for all variables of interest, such as voltage, evaporation rate, and volume change. The neural network can also construct or receive as an input a priority list that assigns an importance factor to each variable to indicate the importance of the variable to the final outcome, or the osmolarity value. The neural network can be configured to construct the calibration curves by training on examples of real data where the final outcome is known a priori. Accordingly, the neural network can be trained to predict the final outcome from the best possible combination of variables. This neural network configuration that processes the variables in an efficient combination can then be loaded into the processing unit residing, e.g., in the measurement chip 701 or the base unit. Once trained, the neural network can be configured in software and/or hardware.

Although the embodiments described above for measuring osmolarity provide substantial advantage over the conventional osmolarity measuring techniques such as a freezing point depression technique, the embodiments described herein can be used to determine osmolarity of a sample in accordance with the freezing point depression technique. Accordingly, the exemplary osmometry system 600 of FIG. 6 can be used to provide an osmolarity value based on the freezing point depression technique.

Such a freezing point depression system involves collecting and depositing the sample fluid in a similar manner as in the steps 1300 and 1302 illustrated in the flowchart in FIG. 13. As noted above, however, the osmometer of the osmometer system can include a cooling device, such as a Peltier cooling device. In the embodiment of FIG. 7 described above, the Peltier device can be disposed on the socket 710 or the chip 701 (see FIG. 7) to cool the sample. If desired, the Peltier cooling device can be used to cool the sample fluid to the freezing point of the sample fluid. A photo-lithographed metal junction, or p-n junction, known as a thermocouple, can be used to monitor the temperature of aliquot-sized samples. The thermocouple can be configured to operate in parallel to the electrode array and Peltier cooling device, where the chip would be cooled below freezing so that the sample becomes a solid. Upon solidification, the electrical conductivity of the sample will drastically change. Because the thermocouple is continually measuring the temperature, the point at which the conductivity spikes can be correlated to the depressed freezing point. Alternatively, the chip can be supercooled immediately prior to sample introduction by the Peltier unit, and then by using the resistive heating inherent to the electrodes, a current can be passed along the solid phase material. Upon melting, the conductivity will again drastically change. In the second measurement technique, it is likely that evaporation will be less of a factor. Thus, the embodiments described herein permit freezing point depression to be performed at significantly smaller volumes of sample fluid than previously possible.

With reference to FIG. 8 above, an embodiment of an integrated circuit comprising a hole 720 was illustrated and described. As described, a hole 720 can be used to allow an aliquot volume of the sample fluid 702, e.g., tear fluid, to be deposited on the sample region 806. In the example of FIG. 8, the hole is configured such that a collection device, e.g., a capillary 808, can be used to deposit the sample fluid 702 onto the substrate 806. In other embodiments, however, hole 720 can comprise a channel configured to receive the sample fluid 702 through capillary action or negative pressure and cause it to be transferred to the sample region 806.

The ability to include such a channel can be important because it can eliminate a step in the process. For example, for the embodiment illustrated in FIG. 8, a two step process is required, wherein the sample fluid 702 is first collected and then deposited onto the sample substrate 806. Such a two step process can be sufficient for many applications; however, for some applications, e.g., involving tear film, such a two step process may not be sufficient. For example, in tear film applications, the amount of fluid can be very small. Accordingly, any loses that occur during the two step process, e.g., due to evaporation, operator error, or the process itself, can cause erroneous results. Accordingly, limiting the chances for such losses can, in certain embodiments, greatly improve the efficiency and accuracy of the test, while simplifying the process.

In order to include such a microfluidic channel, the material selection for the packaging 707 can play an important role. This is because the ability of the substrate to receive the sample fluid will depend substantially on the material chosen. Thus, the material chosen should allow for the rapid collection and transfer of the sample fluid, e.g., tears. Accordingly, in certain embodiments, an appropriate glass or polymeric material can be chosen to allow for the required rapid collection of the associated sample fluid, while at the same time allowing sufficient manufacturing tolerances so that the IC can be manufactured affordably. For example, materials or surface treatments which decrease the contact angle between the fluid, e.g., tears, and the substrate, preferably below 90°. A more detailed description of the materials and material characteristics that can be used is presented below.

Figure 14:
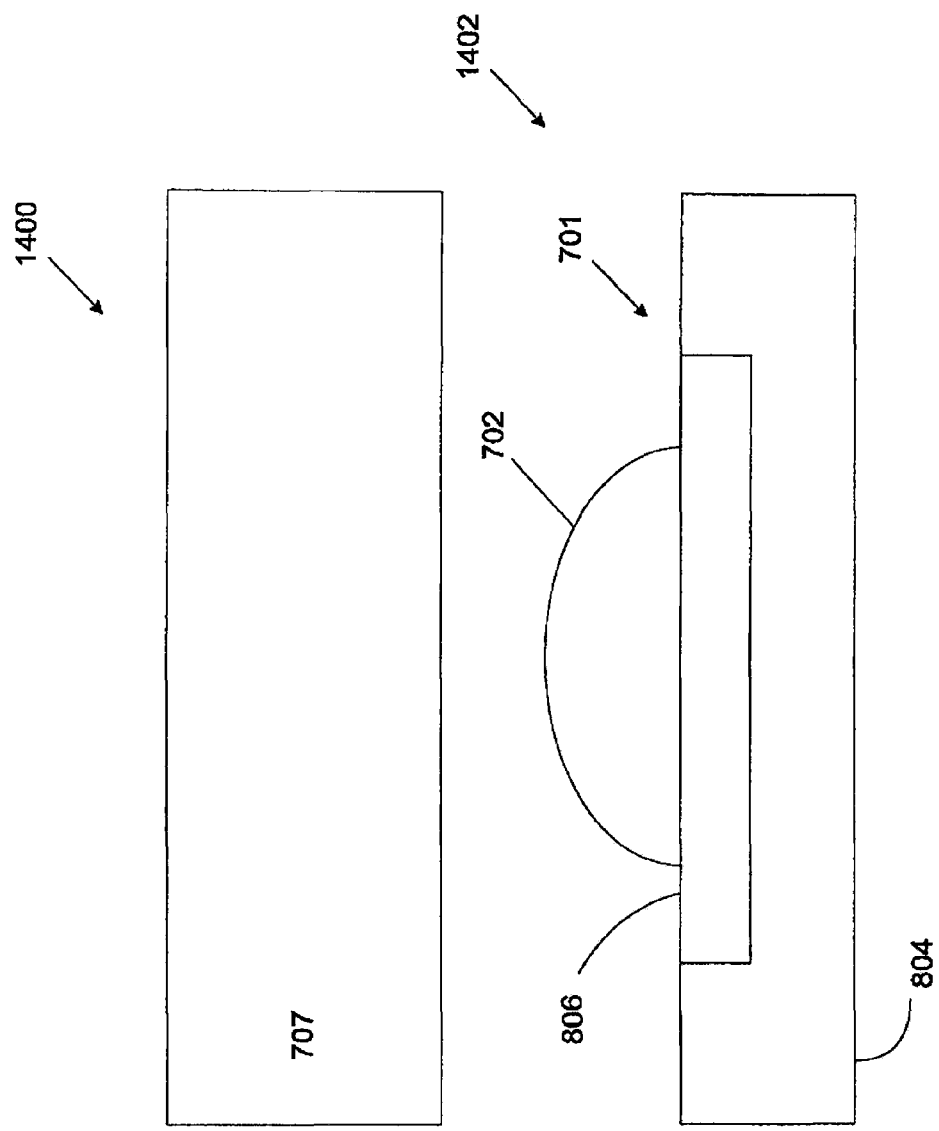
FIG. 14 is a side section of the sample receiving chip showing the opening in the exterior packaging in accordance with another embodiment.

Accordingly, a hole or a channel 720 can become a fluid, or tear collection interface that can be used to receive a sample fluid and transfer it to the sample region 806. It should be noted that the position and geometry of the hole, or the channel 720 can vary in order to optimize the collection and measurement of the sample fluid 702. For example, FIG. 14 is a diagram illustrating an IC 1400 comprising a sample region 701, a transducer within the sample region 806, e.g., electrodes, optical indicators, etc., with the upper strata of the substrate 707 encapsulating the sample region 701 and the lower strata of the substrate 804. In the example of FIG. 14, a channel 1402 is formed in the substrate 804 so as to receive tears, e.g., through capillary action. For example, a channel 1402 can be formed in substrate 804 using various semiconductor manufacturing techniques. As described above, the dimensions and material chosen for the substrate 707 should be selected to ensure rapid collection and transfer of the sample fluid 702 to the sample region 806.

Semiconductor processing techniques can be used to form the channel 1402 residing in the lower strata of the substrate 804. Again, the dimensions and design of the channel 1402 should be selected taking into account the manufacturing tolerances of the semiconductor fabrication techniques being used in order to optimize manufacturability. The design of the substrate should also promote tear collection. For instance, traditional glass capillaries are often pulled to have a circular cross section, with a diameter of less than 300 micrometers (μm) with outer diameters of roughly 1 mm. Such a circular cross section, however, may not be optimal, e.g., for tear collection.

Figure 16:
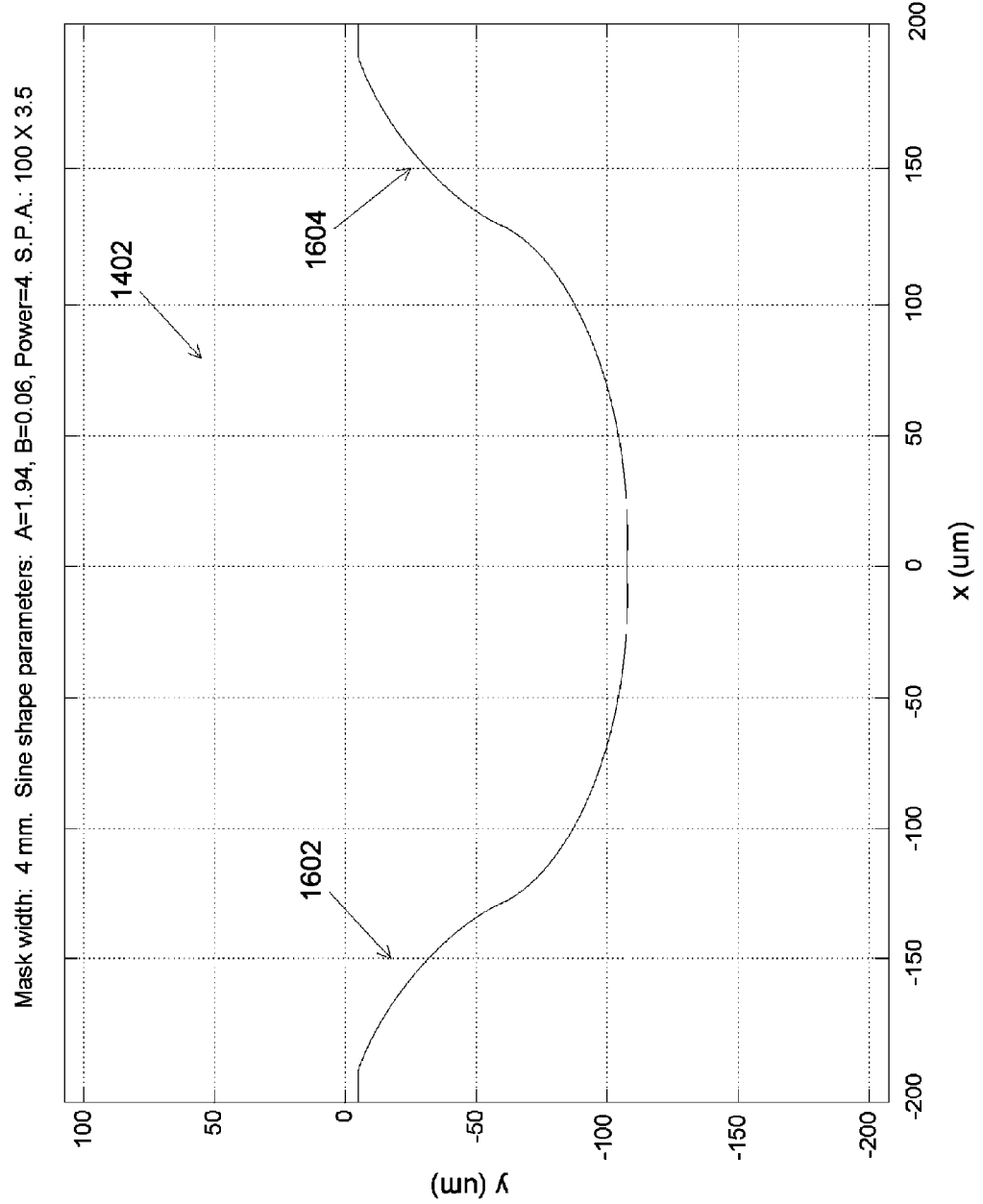
FIG. 16 is a cross sectional view of a channel that can be formed in the receiving chip of FIG. 14.

Accordingly, the channel 1402 can be tapered at each end to improve capillary action. This can also be achieved using a sandwich construction. Such a sandwich construction is shown in FIG. 16, which illustrates a cross sectional view of the channel 1402 in accordance with one embodiment. In the embodiment of FIG. 16, the sloped channel 1402 can be a full width half max dimension of less than approximately 200 μm with a smooth rise at the channel edges 1602 and 1604. Depending on the embodiment, the rise can be sinusoidal, sigmoidal or Gaussian. These embodiments provide drastically shallower channel geometries near the lateral boundary of the channel than the center of the channel. Accordingly, these embodiments should display an increased capillary force at these boundaries, lowering the barrier to capillary action. This provides a substantial benefit over traditional glass capillaries, which feature cylindrical lumens.

The advantages of these geometries include a lower total volume per length of the microchannel as compared to cylindrical channels, as well as the ability to promote tear collection from the inferior fornix also known as the lower tear lake, which is comprised of the thin meniscus of fluid found at the interface between the lower lid and conjunctiva/cornea. These embodiments allow the surface tension of the tear fluid to bridge the opening of the channel when the tear collection interface is placed in the tear lake; fluid will "jump up" to cover the front of the microchannel. Unlike a cylindrical construction where it is often necessary to approach the tear lake perpendicular to the cross section of the lumen, these embodiments promote rotation into the tear lake or resting the tear collection interface on the lower lid which then allows the surface tension to bridge the opening of the lumen.

In other embodiments, the channel 1402 can comprise a triangular cross section, a rounded triangle cross section, a half circle cross section, etc. In fact, the channel 1402 can comprise any geometry that promotes fluid collection.

Other limitations of traditional capillaries are also overcome through the substrate configurations noted herein. For instance, the needle-like appearance of a glass capillary is suboptimal for patient interaction. In accordance with the embodiments described herein, the substrate can be made rounded or more blunt edged to be more inviting to the patient, and can be made of softer materials, i.e., polymer, to eliminate the chance of injury to the corneal surface. Furthermore, the edge of the substrate can be configured to be very thin near the opening of the channel to promote entrance into the tear lake. For example, in one embodiment the sample receiving chip can be placed parallel to the lower lid and then rotated upwards such that the tip of the substrate touches the tear lake as described in more detail. By fashioning the substrate such that the upper strata covering the channel is minimized in vertical extent, preferably less than approximately 100 µm, the substrate can be rotated into the tear lake and the lumen of the channel can be completely covered with tear, even if the entirety of the substrate is not wetted. The lower strata of the substrate can also be configured for mechanical stability.

These techniques are not possible with traditional glass capillaries, which are radially symmetric and lose mechanical stability as the lumen of the capillary approaches 100 µm. In this case, collection of small nanoliter volumes presents undue risk to the patient as a properly timed blink could break off the tip of the glass capillary and introduce shards of glass into the patient's eye. Asymmetrically configuring the strata of the substrate provides both the ability to use rotational tear collection as well as superior mechanical stability, capillary action, and patient interaction as compared to traditional tear collection methodologies. These embodiments are particularly useful when the patient lacks a substantial volume of tear on their ocular surface.

The substrate can also be configured to promote capillary action by having a curved shape having an apex or rounded peak so that the substrate can be moved proximate the eye surface, to pull in tear fluid via capillary action. The curved shape can be configured to minimize the substrate area that comes close to the eye, thereby minimizing any contact with the eye and making it easier for the clinician to get close to the eye and collect the fluid. The apex of the curve can include a feature to promote capillary action and receive the fluid. For example, FIG. 17B shows that a channel 1402 in the substrate 1704 extends to the edge of the shape, at the apex. Placing the edge of the substrate 1704 proximate the eye surface allows tear fluid to enter the channel 1402 (see FIG. 17C), utilizing a capillary action.

It will be understood that conventional semiconductor manufacturing techniques can handle such dimensions and features. Thus, the channel 1402 can be patterned and formed, e.g., using an excimer laser, Nd-YAG laser, or photolithography. The material chosen should then be amenable to the process being used.

It should be noted that the upper strata of the substrate 707 can be formed such that channel 1402 extends to the edge of the substrate. In this way, the IC 1400 can act as the receiving substrate for collecting sample fluid 702. Thus, rather than using a separate collection device, such as a glass capillary to collect the fluid, the IC 1400 can be used for collection and measurement. Thus, the IC 1400 can comprise a substrate that promotes tear collection. The IC 1400 can then be interfaced with a processing device, such as device 606, or in other embodiments, removed from the collection device and interfaced with a processing device.

Figure 17A:
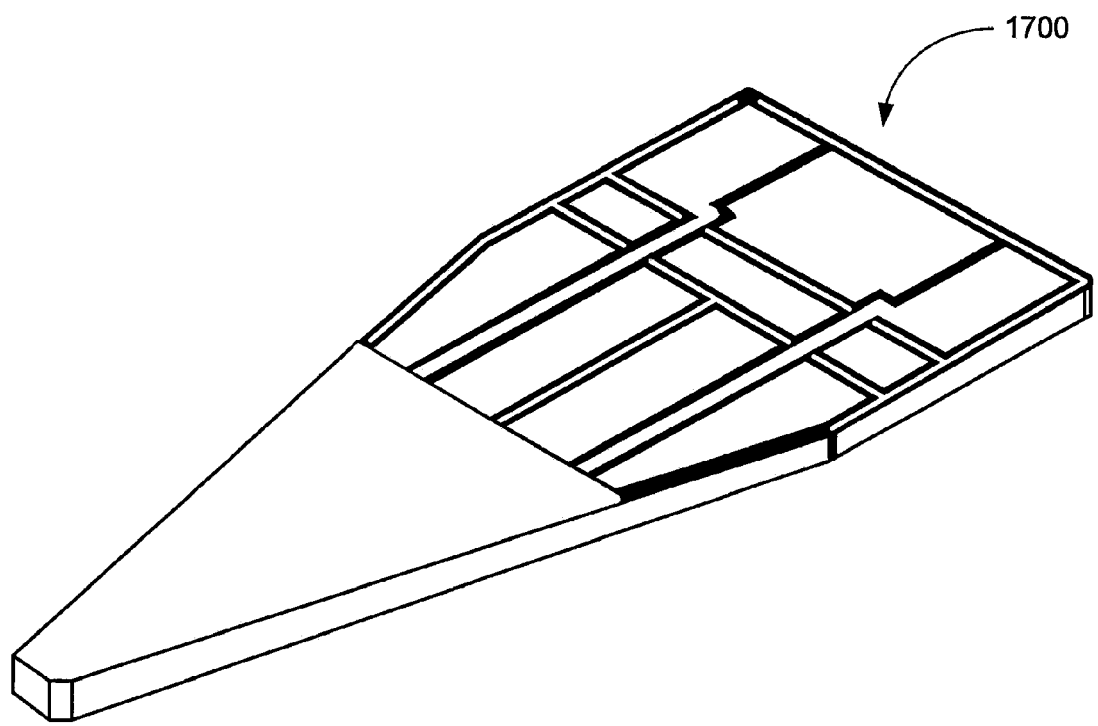
FIG. 17A illustrates a microfluidic collection device in accordance with one embodiment.
Figure 17B:
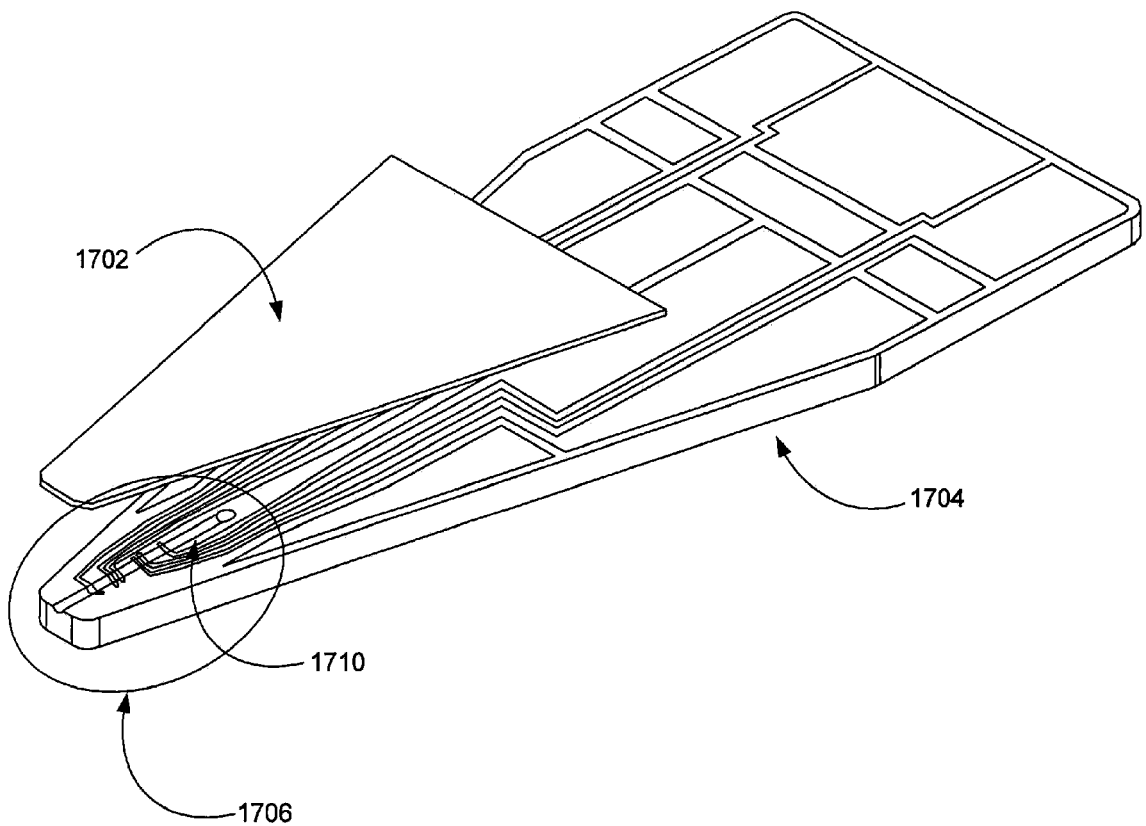
FIG. 17B illustrates a more detailed view of the device of FIG. 17A.
Figure 17C:
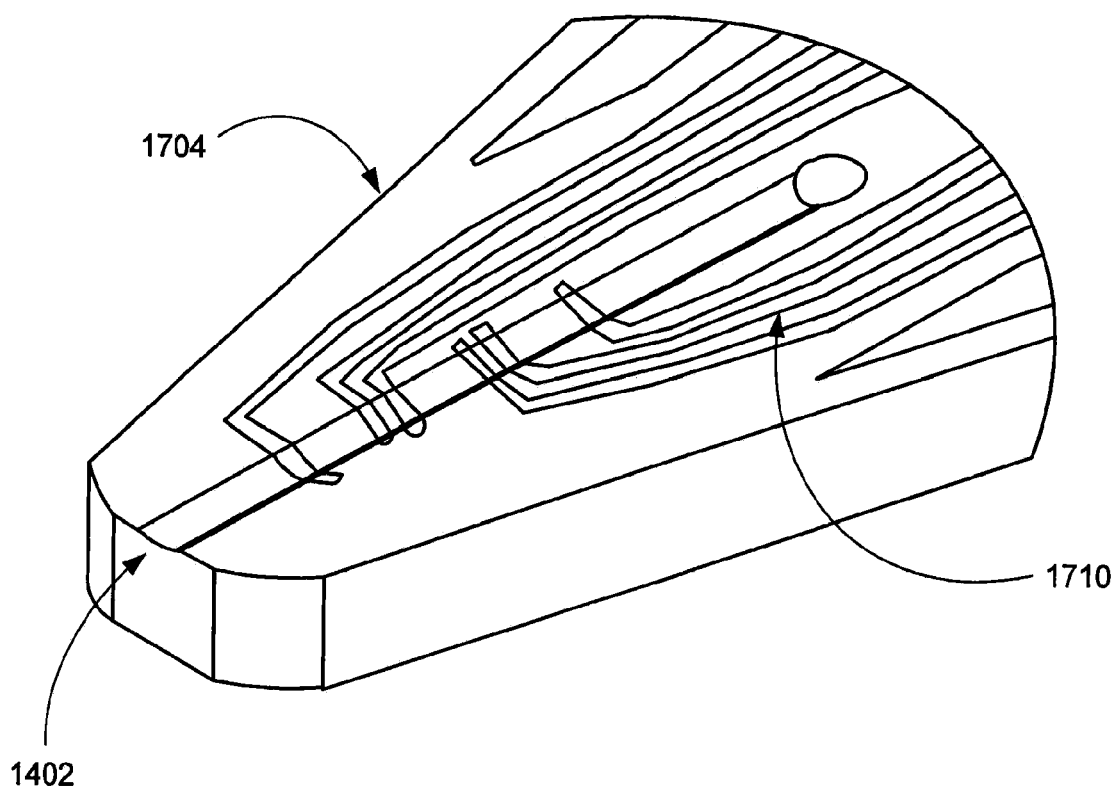
FIG. 17C illustrates an exploded view of a portion of the device of FIG. 17B.

FIGS. 17A-17C are diagrams illustrating example embodiments of a configured in accordance with one embodiment. Integrated circuit 1700 can comprise a substrate 1704, which can include a sample region 1706, which is shown in finer detail in FIG. 17C. The substrate 1704 can also include a channel 1402 and electrodes 1710. The upper strata of the substrate 1702 can be placed over the lower strata of the substrate 1704 as illustrated in FIG. 17A. As can also be seen in FIG. 17B, the channel 1402 can extend to the edge of the device 1700 so that the substrate 1704 can receive an aliquot volume of tear and transfer the fluid to the sample region 1706 for measurement. Note that the substrate 1704 is shaped to promote capillary action from the tear lake as described above. The curved edge of the substrate 1704 with the channel 1402 placed perpendicular to the tangent of the curved edge promotes capillary action within the tear lake with minimal risk to the patient. The substrate shape includes the curved edge of the substrate 1704, the appropriate thickness of the strata 1702 and 1704, and the cross section of the substrate channel 1402. The substrate shape can also comprise a short, blunt end with channel 1402 perpendicular to the blunt end, and then a linearly receding substrate to form a rectangularly or triangularly receding shape to the substrate 1704.

The substrate 1704 can also be shaped to promote easy placement near the eye surface, such that the sample receiving chip can be rotated, dipped, pressed, or linearly translated into the tear lake while exposing the channel edge of the substrate to the tear lake. The substrate can also be shaped such that it is gently angled to allow the channel to protrude slightly, which allows a thinner extent that makes contact with the tear lake. Since the channel 1402 extends from the sample region 1706 to the edge of the substrate at the rounded edge, the shape of the substrate therefore promotes wicking through capillary action from the edge to the sample region.

FIG. 17B is a diagram illustrating a blown up view of area 1706 in FIG. 17A. As can be seen, electrodes 1710 can be formed over substrate 1704 and in contact with channel 1402 in the sample region. FIG. 17B also more clearly illustrates that channel 1402 extends to the edge of substrate 1402, and therefore the edge of device 1700.

It should be noted that channel 1402 does not necessarily need to have the shape and geometry illustrated in FIGS. 17A and 17B. As mentioned above, the channel 1402 can comprise any one of various cross section dimensions and in general, the channel 1402 can comprise any geometry that promotes fluid collection. Moreover, the channel 1402 can actually comprise any modification to the surface of substrate 1702 that performs the functions of fluid collection.

In the example embodiment of FIGS. 17A and 17B, the upper strata of the substrate 1704 can be made from a polyester film and attached via a hydrophilic adhesive applied to the bottom side of the substrate 1704. The substrate 1704 can be formed from a polycarbonate material or other material compatible with semiconductor fabrication techniques. The substrate materials are preferentially hydrophilic, although a sandwich construction (see FIG. 16), where a hydrophilic layer seals a more hydrophobic channel, or hydrophobic sealant of a hydrophilic channel, can also be made to wick tears; glass on polyimide, for instance. The classes of materials that are preferable for the substrate include glass, hydrophilic polymers, silicon, di- and triblock copolymers with amides, amines, sulfates, phosphates or other charged groups. For instance, polyether block amides (PEBA), block-copolyether-esters (PEE), polylactic acid (PLA), polyurethanes (PU) including aliphatic and thermoplastic polyurethanes, polyglycolic acid (PGA) and other polyesters (PE), polycaprolactone (PCL), polyethersulfones (PES), polycarbonate (PC) or any other combination of hydrophilic copolymers which demonstrate proper manufacturing stability and contact angle which promote tear collection.

Other means of constructing a heterogeneous substrate include a stratified stack of materials that promote wetting at the tear film interface as well as hydrophilicity throughout the extent of the sample receiving region of the substrate 1402. For instance, in one embodiment, a hydrophilic pressure sensitive adhesive (PSA) is used to seal a polycarbonate channel to a glass cover slip, such that the strata (glass, PSA, polycarbonate) decrease in hydrophilicity, yet when placed in the tear lake, the tear fluid readily wets across the lumen of channel 1402. In such an embodiment, the upper strata of the substrate 1702 can be made of any of the aforementioned materials, which reduce surface tension and promote wetting when placed in contact with the tear film. Similar configurations are possible when making the lower strata of the substrate 1704 hydrophilic through intrinsic material properties or surface treatments.

Figure 18:
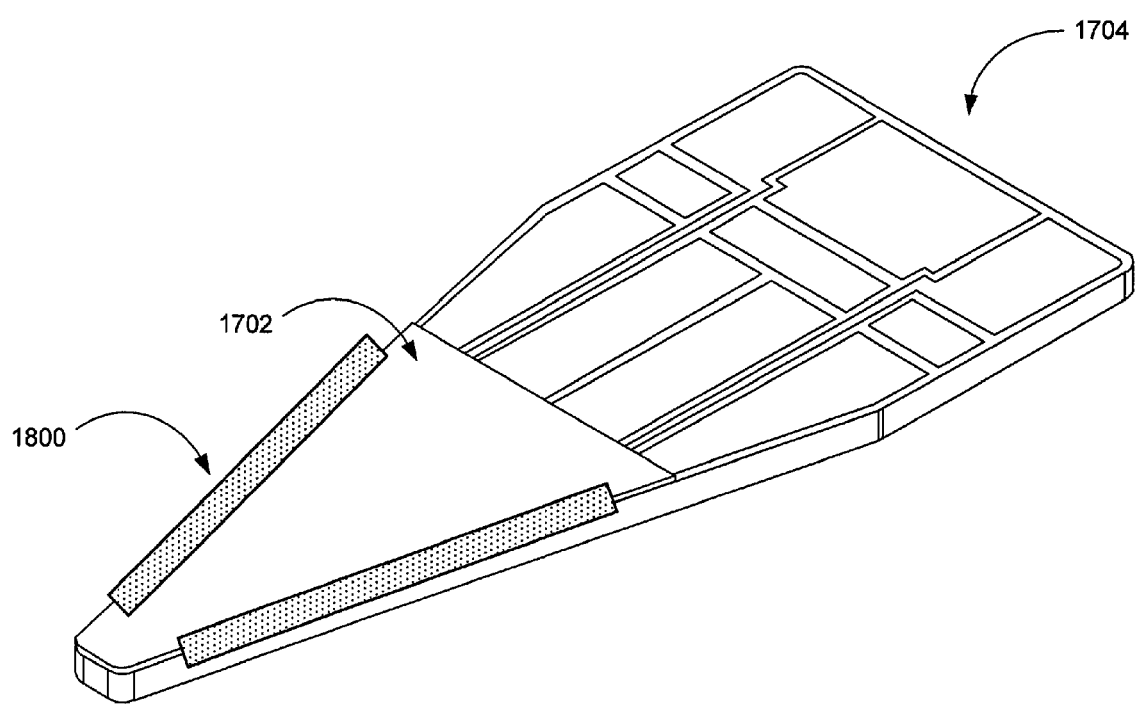
FIG. 18 is a diagram illustrating another example embodiment of a microfluidic collection device.

In other embodiments, a polycarbonate substrate adhered to a hydrophilic PSA comprised of, e.g., 25 μm polyester-based hydrophilic adhesive with a, e.g., 100 μm polyethylene terephthalate (PET) backing can be used. To complete the stack, a hydrophobic adhesive can be applied around the outside of the substrate 1714 to eliminate the flow of tears around the exterior of the substrate 1704. Such an embodiment is pictured in FIG. 18, with the substrate 1704, the hydrophilic PSA 1702, and the hydrophobic adhesive 1800 pictured. The hydrophobic adhesive can be comprised of, e.g., beeswax, epoxy resins, or UV curable resins such as urethane (meth)acrylate, and the like. The absence of adhesive 1800 can allow tears to flow around the exterior of the substrate 1704 and short out the electrodes at the back of PSA 1702.

In another embodiment, the tear collection interface can use the sigmoidal, sinusoidal, or semicircular channel from the PSA backing and hydrophilic PSA adhesive, with the electrodes residing on a flat polycarbonate substrate.

Another embodiment of hydrophilic strata uses identical material on the upper and lower strata but includes a hydrophilic layer in the middle, in direct contact with the channel lumen 1402. This can be a less expensive construction. Amphiphilic polymer constructions can also be used, where hydrophobic side chains are used to bond strata together, while exposing hydrophilic side chains to the channel interior.

Modifications to one or more of the material layers can also promote tear collection, such as plasma etching, with nitrogen, oxygen, argon or other gaseous plasmas, acid treatment, exterior coating, increases in surface roughness on the micro- or nanoscale, or comparable methods that reduce contact angle. For example, polyelectrolyte coatings comprising polyethyleneimine, polyaminoalkyl methacrylate, polyvinylpyridine, polylysine, polyacrylic acid, polymethacrylic acid, polysulfonic acid, polyvinyl sulfate, polyacrylamido-2-methyl-1-propanesulfonic acid, and polystyrene sulfonic acid, or other coatings or resin additives known to increase charge density at the interface. In general, any material, e.g., polymer, resin, glass, etc., can be used for the substrate 1702 that can promote capillary action at the edge of the sample receiving chip.

Figure 15:
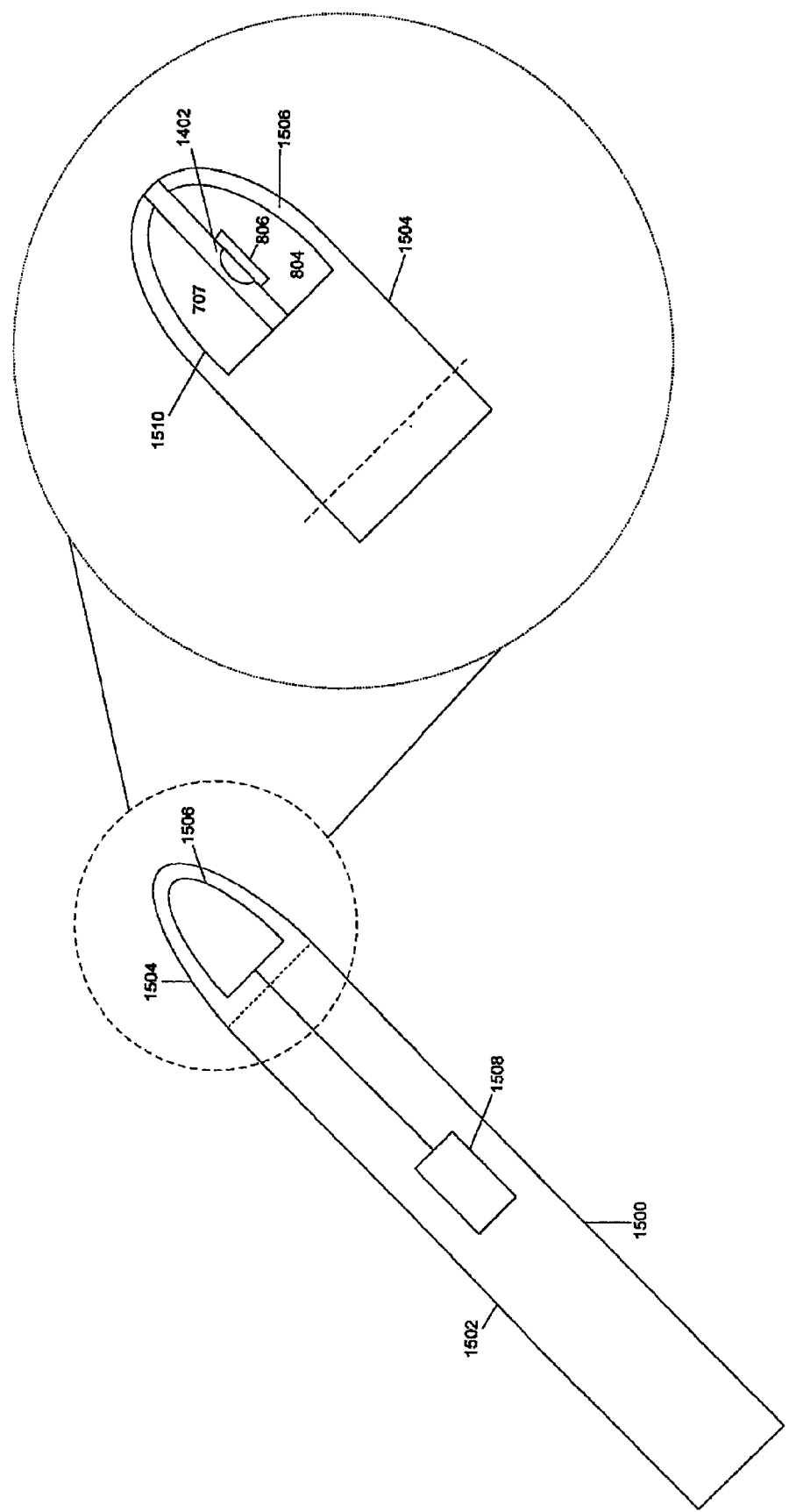
FIG. 15 illustrated an example collection device that can hold the receiving chip of FIG. 14.

FIG. 15 is a diagram illustrating an example of the collection device 1500 comprising, e.g., a sample receiving chip 1700 in accordance with one embodiment. Device 1500 can, for example, be sized and shaped somewhat like a pen and can comprise a base portion 1502 and a tip portion 1504 configured to house the sample receiving chip 1700. The tip portion 1504 can be configured so that it can be placed in contact with the sample fluid allowing channel 1402 to collect an aliquot volume of the sample fluid for testing. Tip portion 1504 can be configured so that it can then be removed and interfaced with a processing unit 606, thereby interfacing device 1700 with processing unit 606 so that the osmolarity of the sample fluid can be measured as described above. Thus, collection device 1500 can include a mechanism (not shown) for decoupling, or ejecting tip portion 1504. Collection device 1500 can also be a blunt ended, flat device that seems less needle like to the patient and uses a hinge mechanism to receive device 1700.

In certain embodiments, tip portion 1504 and/or device 1700 can then be disposed of and base portion 1502 can be reused with another tip portion 1504 and/or device 1700. Methods such as those described above can then be used to ensure that a previously used device 1700 is not reused.

Further, an informational signal 1508 can be integrated within collection device 1500 and configured to indicate whether the substrate is properly connected and whether enough sample fluid has been collected. For example, fluid filled electrodes, e.g., the outermost electrodes shown in FIG. 17A, i.e., closest to the channel opening, and closest to the vent hole, can provide a convenient transducer within the substrate. A 2-point impedance measurement across these electrodes can distinguish between an open circuit device, and an attached substrate with an empty channel, with typical impedance values changing from around 5 MOhm to around 1 MOhm upon connection of the substrate to the device. Tear collection reduces the impedance between the fluid fill electrodes to generally below 100 kOhm at 100 kHz, providing two clear thresholds for hardware to provide user feedback.

Indicator 1508 can also include, or be coupled with an auditory indicator to indicate whether enough sample fluid has been collected. For example, a Light Emitting Diode (LED) or other indicator can be activated when enough sample fluid is present. A beep or other tone in conjunction with the visible feedback can be used as parallel indication of filling the channel. Alternatively, one indicator, such as a red LED, can be included to indicate that not enough sample fluid is present, and a second indicator, such as a green LED can be used to indicate when enough sample fluid is present. Thus, for example, the red LED can be active until enough sample fluid is present at which point the red LED is turned off and the green LED is activated.

In other embodiments, audible indicators can be used. In still other embodiments, displays such as LED or Liquid Crystal Displays (LCDs) can be used to convey the sample fluid status.

Pen device 1500 and the methods described herein can be used to collect nanoliters of tears from the inferior meniscus, located between the lower lid and conjunctiva/cornea. Other potential embodiments of a pen device are described in detail below. More specifically, the devices and methods described herein relate to materials, manufacturing processes, and geometries specific to collection devices for the repeatable, non-invasive collection of tear film. These devices and methods represent a significant departure from the clinical standard of care; the glass capillary. By using the materials and methods described herein, a CLIA waivable interface for tear collection can be achieved.

Figure 21:
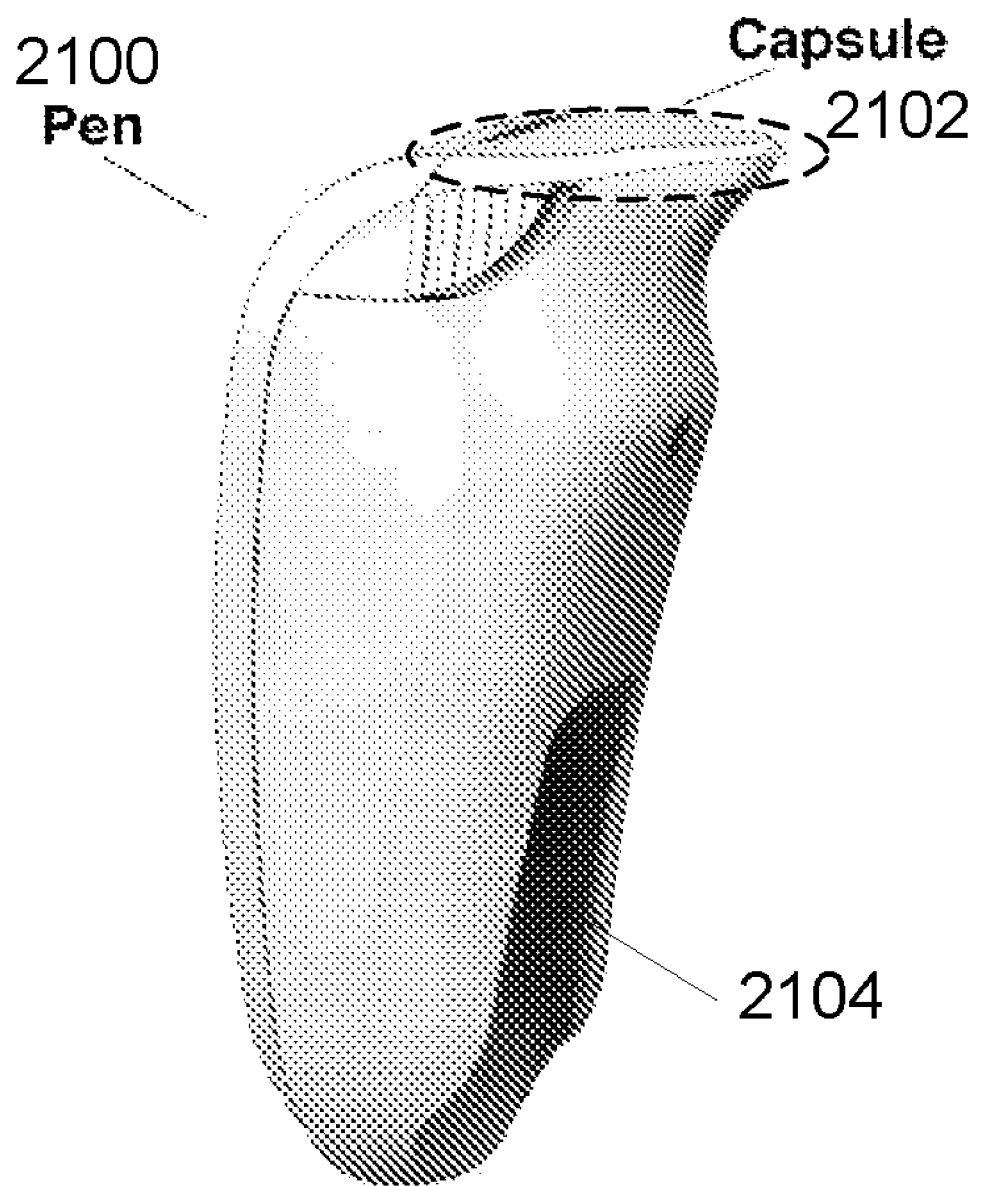
FIG. 21 is a diagram illustrating an example pen like collection device that includes a body and a capsule, the capsule configured to hold a sample receiving chip such as illustrated in FIGS. 17A-17C.
Figure 22:
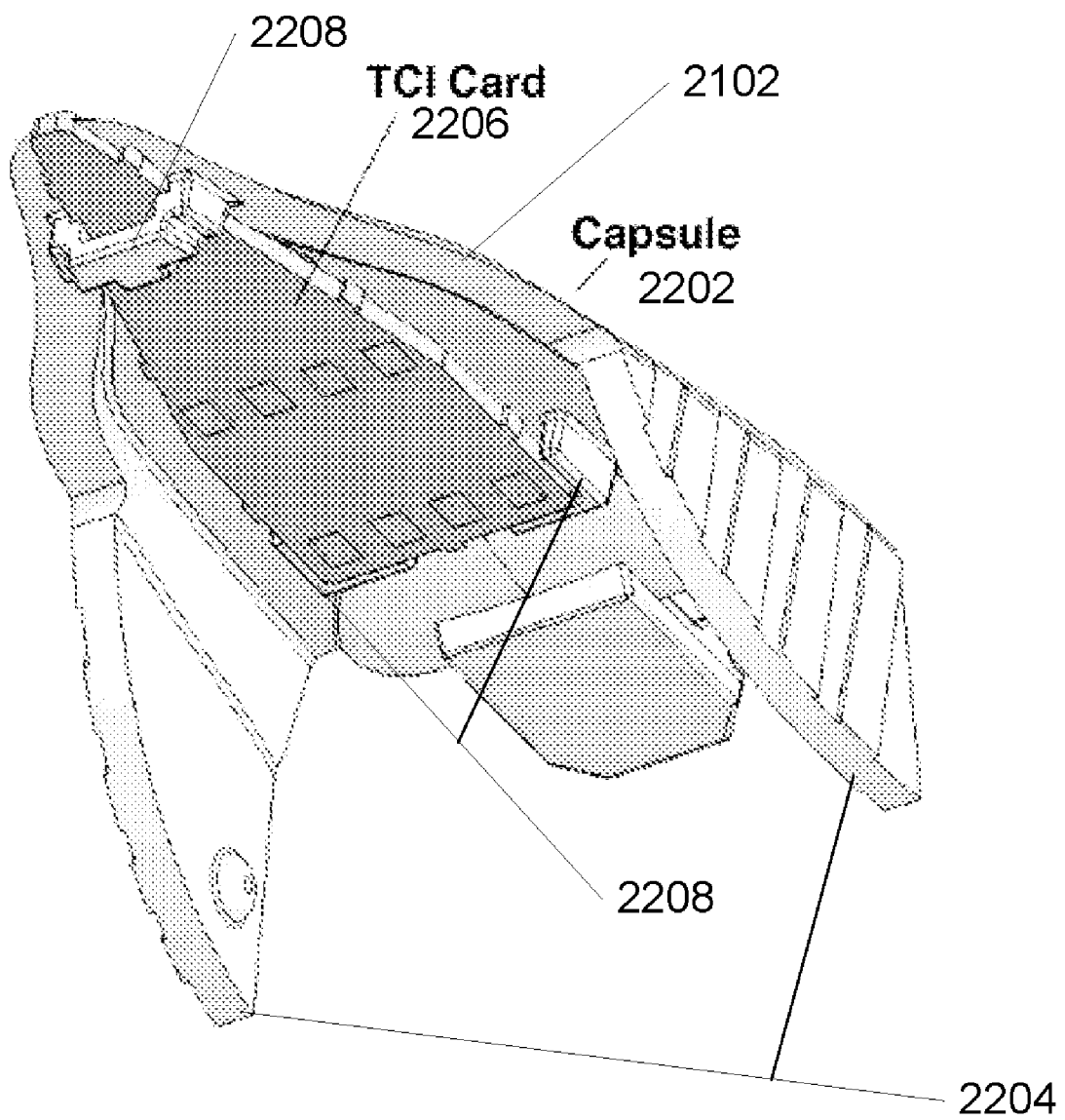
FIG. 22 is a diagram illustrating the capsule of FIG. 21 in more detail.
Figures 23A, 23B:
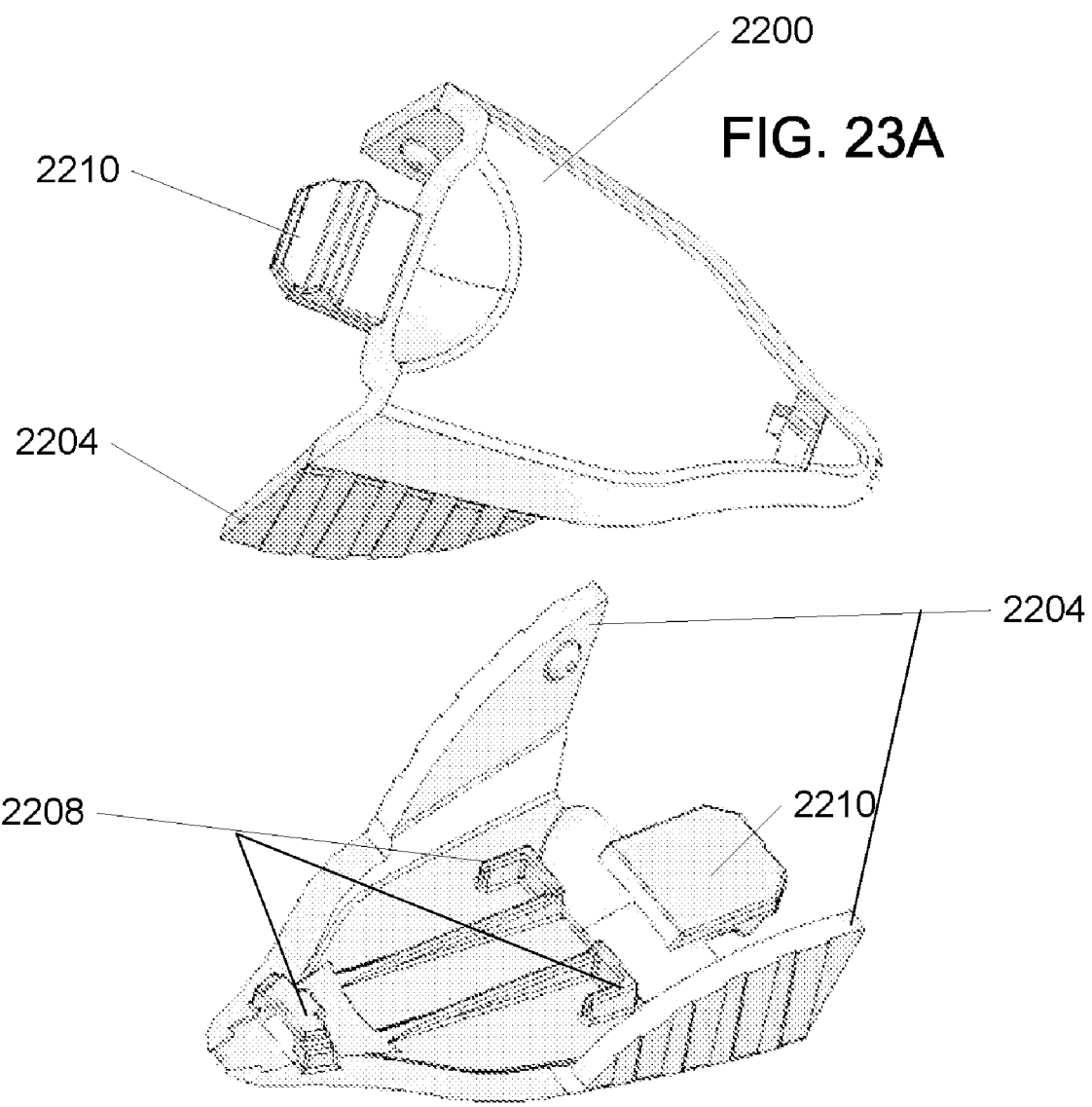
FIGS. 23A and B are diagrams illustrating alternate views of the capsule of FIGS. 21 and 22.

For example, FIG. 21 is a diagram illustrating an alternative embodiment of a 'pen device' 2100 configured in accordance with one embodiment. In this embodiment, pen 2100 can act as an intermediate holder of a tear collection interface (TCI) card (see 2206 in FIG. 22) and capsule (see 2202 in FIG. 22) (collectively 2102). TCI card (2206) can consist of a receiving substrate, sample region, and means of energy transduction as described above. For example, TCI card 2206 can comprise a polycarbonate substrate containing a nanofluidic channel with embedded gold electrodes and capped by a hydrophilic pressure sensitive adhesive. Capsule 2202 can be a mechanical interface between the generally flat receiving substrate of TCI card 2206 and pen 2100. For instance, electrical contacts through a SIM connector, or a spring loaded array of metal wires can serve as an opposing force to the capsule location features through the springs of the contacts to provide a solid connection to the pen body, e.g., the springs push up on capsule 2202 and the hooks 3302 at the front of the capsule (see FIG. 33A) are pulled down by the front of Pen 2100, thereby providing a reliable electrical and mechanical interface between capsule 2202 and Pen 2100. Similar mechanical features may use the elasticity in fluidic gasket seals to act as a counterbalance. Robust connections in this manner also ensure optical signals (e.g., waveguides, optical isolation points, etc.) are aligned and maximally coupled.

For example, TCI card 2206 can be similar to sample receiving chip 1700 illustrated in FIGS. 17A-17C.

In one specific embodiment, capsule 2202 can comprise a plastic protective case 2200 with finger grips 2210 and tabs 2208 on the underside to hold TCI card 2206 in place. Capsule 2202 can also provide a connection means to pen 2100, such as through somewhat elastic, grooved wings 2204 along the outside edge, or other common connection means, such as magnetic, slotted, or screw mounts. Features in the pen/capsule interface can include a space for a vent hole at the bottom of TCI card 2206, which, when sealed from the top, requires an exit hole to permit capillary action to wick tears into card 2206 as described above.

Pen 2100 can also provide electrical, optical, and fluidic connections at the capsule/pen interface, through the body 2106 of pen 2100, and out to a base unit (not shown), when used in conjunction with a processing device to perform precision analytics on the sampled tears. To this end, a recessed cutout 2104 can be included in body 2106, e.g., in the lower portion of pen 2100. Such a feature can be referred to as a "dove-tail" connector. The dove-tail can enable secure connection to a processing device, while insulating any related contacts from user interaction.

Figure 24A:
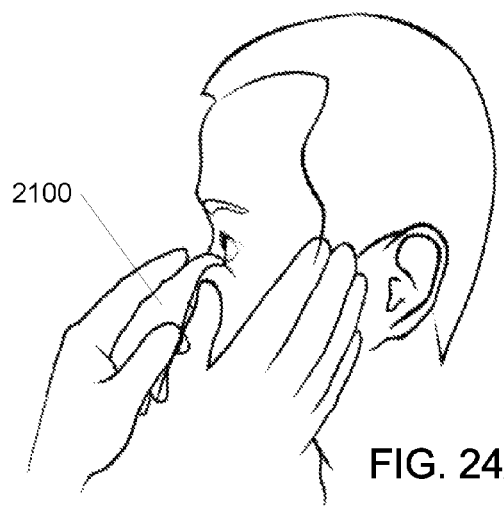
FIGS. 24A and B are diagrams illustrating example methods for using the device of FIG. 21 to collect tears.
Figure 24B:
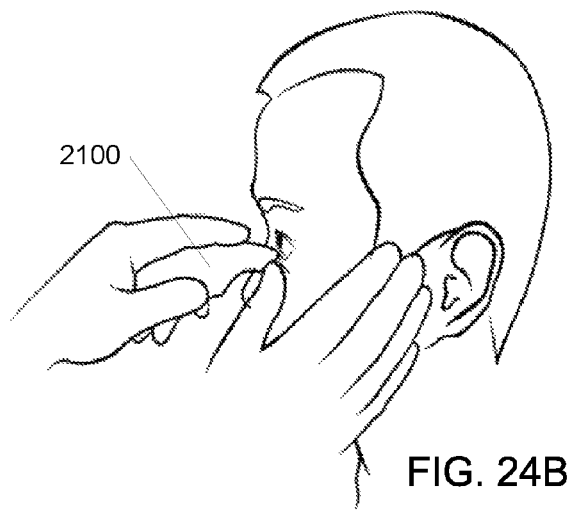
Figure 25:
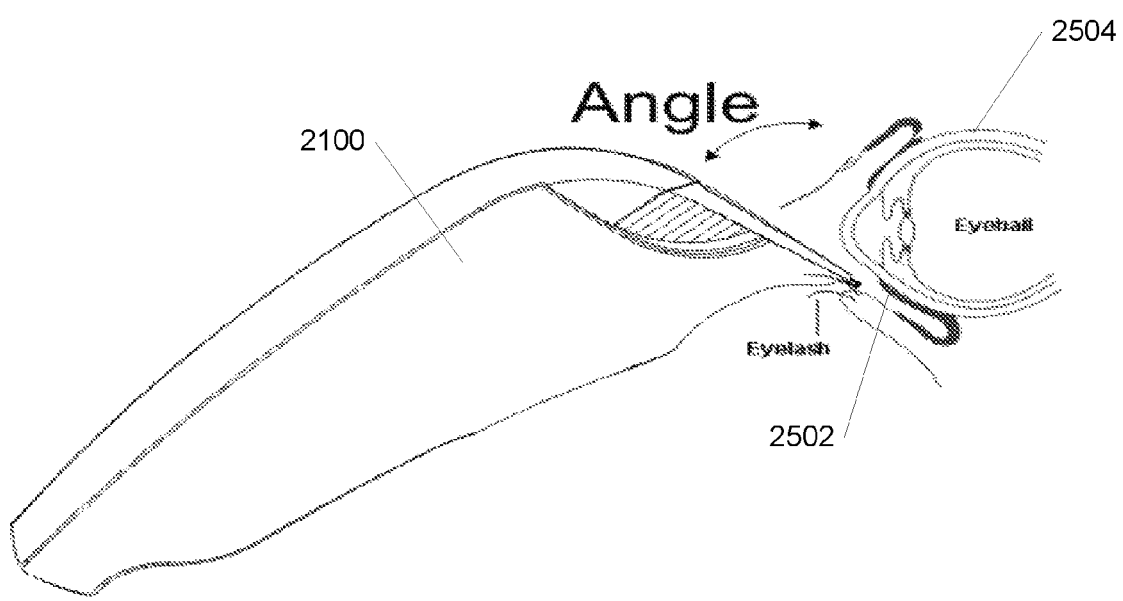
FIG. 25 is diagram illustrating a detailed view of the device of FIG. 21 being used to collect teas form the meniscus.

Collection of tears from the eye is accomplished by rotation of pen 2100 against a fulcrum, which can, e.g., consist of an opposing thumb and gripping forefinger on pen 2100, or lower orbital bone as illustrated in FIGS. 24A and B. A gross rotation of the handle of pen 2100 can be converted into a fine linear translation into the inferior tear meniscus 2502 (see FIG. 25); in this way untrained users can achieve fine movements at the ocular surface of the eye 2504. For example, depending on the embodiment, a 30° rotation of the pen handle can result in a linear translation of a few millimeters into the tear lake 2502. This operation is in contrast to the clinical standard glass capillary tube, which requires a steady hand to guide into the interface between tear film and conjunctiva. Moreover, the aspect ratio of the pen can be designed to be aesthetically non-threatening as compared to the needle-like appearance of glass capillary tubes. The ergonomics of pen 2100 can help ensure that blinking or sudden movements during tear collection do not injure the patient.

Figure 26A:
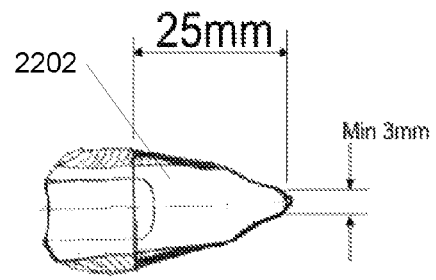
FIGS. 26A-C are diagrams illustrating the pen device of FIG. 21 in more detail.
Figure 26B:
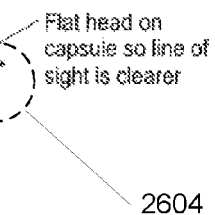
Figure 26C:
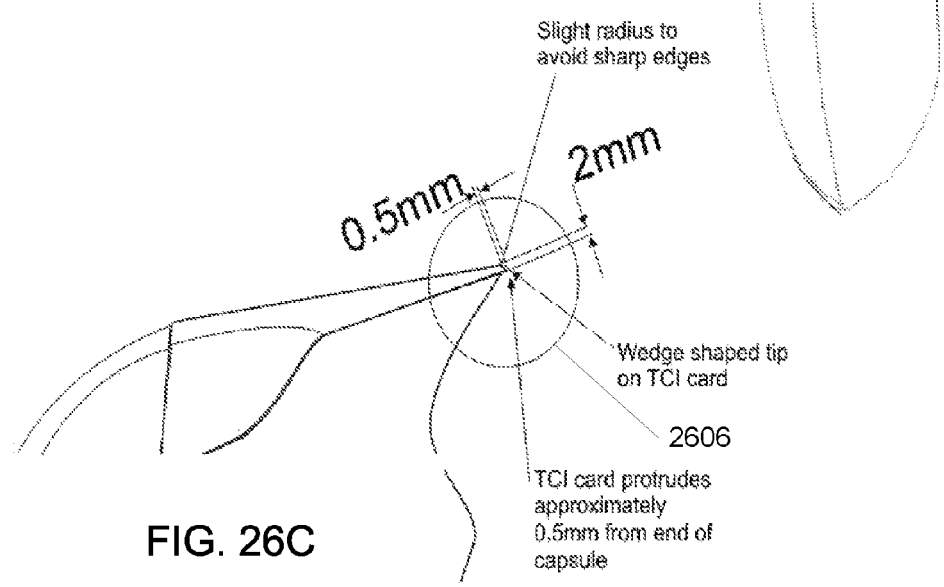

FIGS. 26A-C are diagrams illustrating one example embodiment of pen 2100. As can be seen in FIGS. 26A and B, capsule 2202 can, e.g., be about 10-30 mm long, with a linear taper followed by a concave cutaway 2602, and a convex tip 2604 at the ocular surface. Convex tip 2602, of roughly 3 mm width can be configured to soften the entrance to the tear lake and can also be designed to be aesthetically pleasing to the patient. The flat head on capsule 2202 and cutaways 2602 can give a clear line of sight into the meniscus during tear collection. The TCI card tip 2606 can be configured to protrude on the order of, e.g., 0.5 mm from the convex end of the capsule as illustrated in FIG. 26C.

In one specific embodiment, capsule 2202 can be approximately 25 mm long and tip portion 2602 can be approximately 2 mm long.

Again, as described above, the receiving substrate on TCI card 2206 can be configured to wick tear fluid into the nanofluidic channel for physicochemical, biochemical, or multiplexed analysis.

The ambidextrous design of pen 2100 supports a variety of hand positions. Thus, e.g., a user can choose a pistol type grip, where the thumb is on top of the capsule and the forefinger is in the convex portion 2604. Other possible grips include a traditional pen-type grip, or a side-pistol grip with the forefinger on top. The beveled backside of pen 2100 contributes to the versatility of the design, as does the convex backplane and rounded bottom of the pen.

Figure 27:
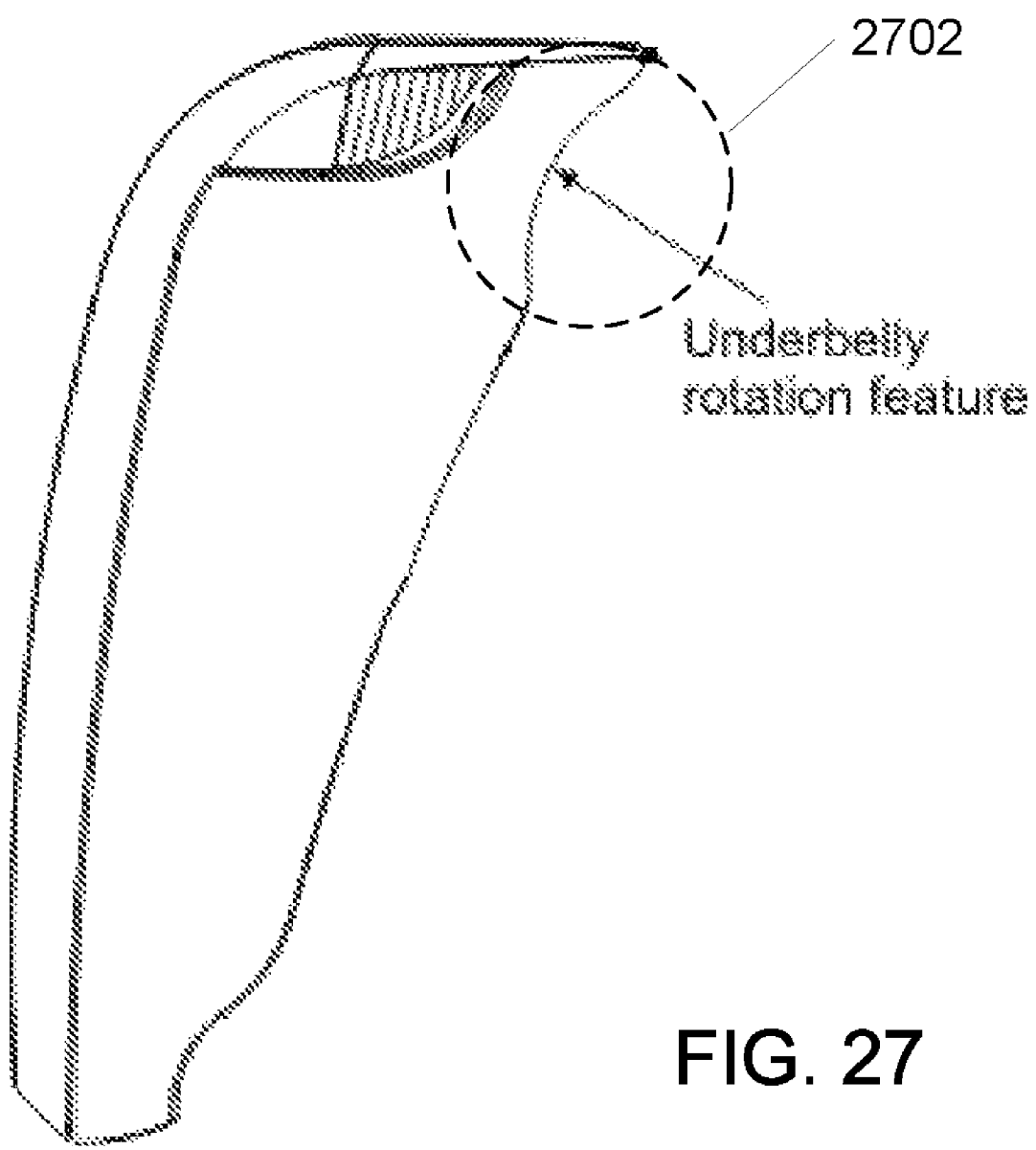
FIG. 27 is a diagram illustrating a rotational feature of the pen device of FIG. 21.

FIG. 27 demonstrates an example projection of pen 2100 with the underbelly rotation feature 2701 highlighted. The underbelly rotation feature 2701 allows the thumb or forefinger to comfortably act as a point of rotation, or fulcrum, during tear sampling. Various shapes of the underbelly rotation feature are possible. Depending on the embodiment, users can choose a different type of pen head based on grip preference, hand size, or TCI card type.

Figure 28A:
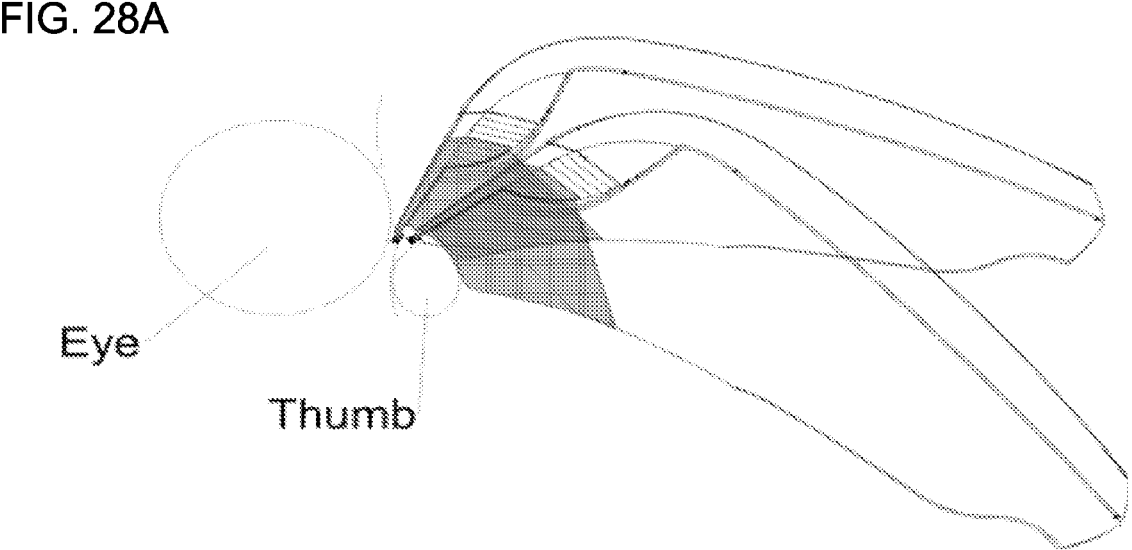
FIGS. 28A and 28B are diagrams illustrating alternative embodiments of the rotational feature of FIG. 27.
Figure 28B:
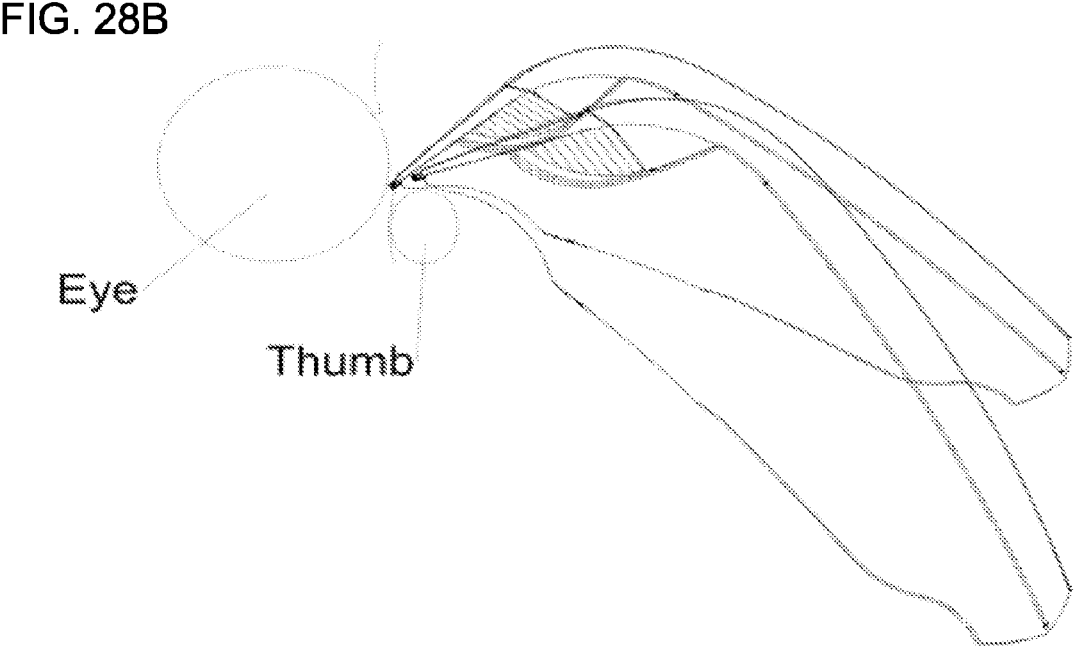

FIG. 28 shows the effect of different underbelly rotation features. In FIG. 28A, a steeper underbelly feature 2802 changes the rotation/translation mechanics of pen 2100. FIG. 28B shows a longer underbelly feature 2804, which is amenable to two-axes rotation during tear sampling, and is less restrictive in its use.

FIGS. 29-32 show other possible pen underbelly and capsule taper designs. Each underbelly and capsule design has unique line of sight and rotational possibilities.

Figure 29B:
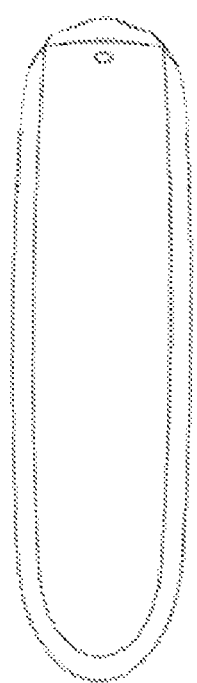
FIGS. 29-32 are diagrams illustrating alternative embodiments of the pen device of FIG. 21.
Figure 29A:
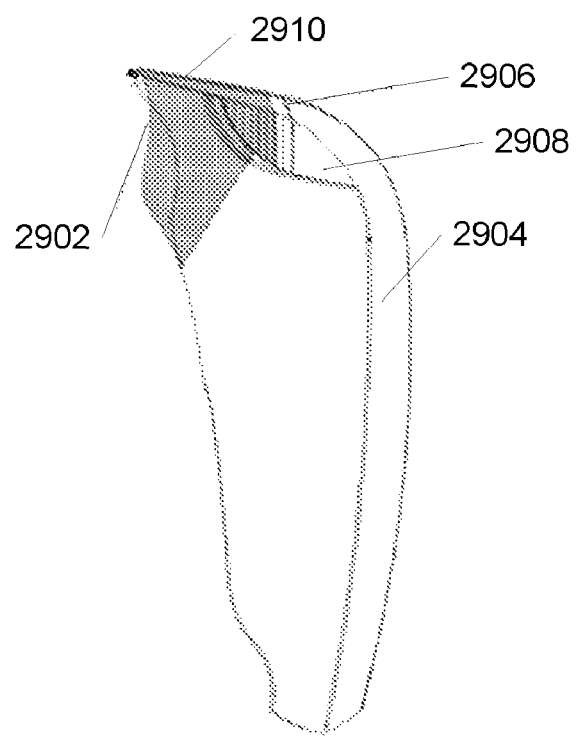
Figure 29C:
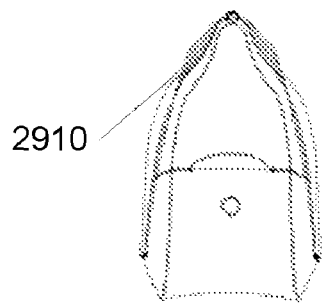

For example, the shaded portion of FIG. 29A illustrated that the pivot point, or underbelly feature 2902 can be decreased, which can, e.g., allow for additional internal components. Also, the finger grips 2908 of pen body 2904 can be increased by decreasing the side grips 2906 of capsule 2910. The shaded portion of FIG. 29C illustrates that a portion of capsule 2910 can also be widened to accommodate additional internal components. FIG. 29B illustrates the sightlines of the design illustrated in FIG. 29.

Figure 30:
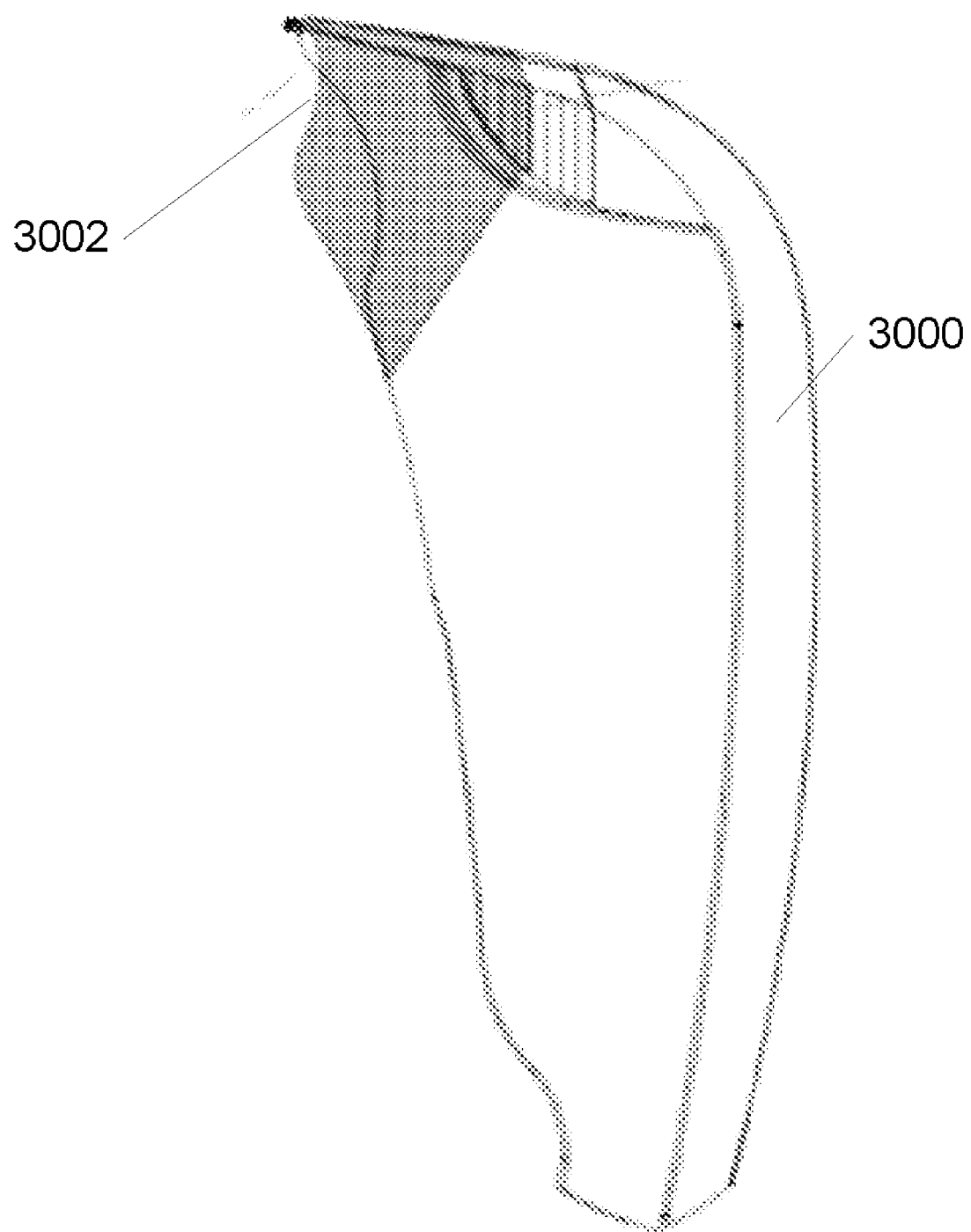

The shaded area of FIG. 30 illustrates an embodiment that comprises a reduced pivot point 3002, which can lead to an alternate motion as pen 3000 moves toward the eye.

Figure 31:
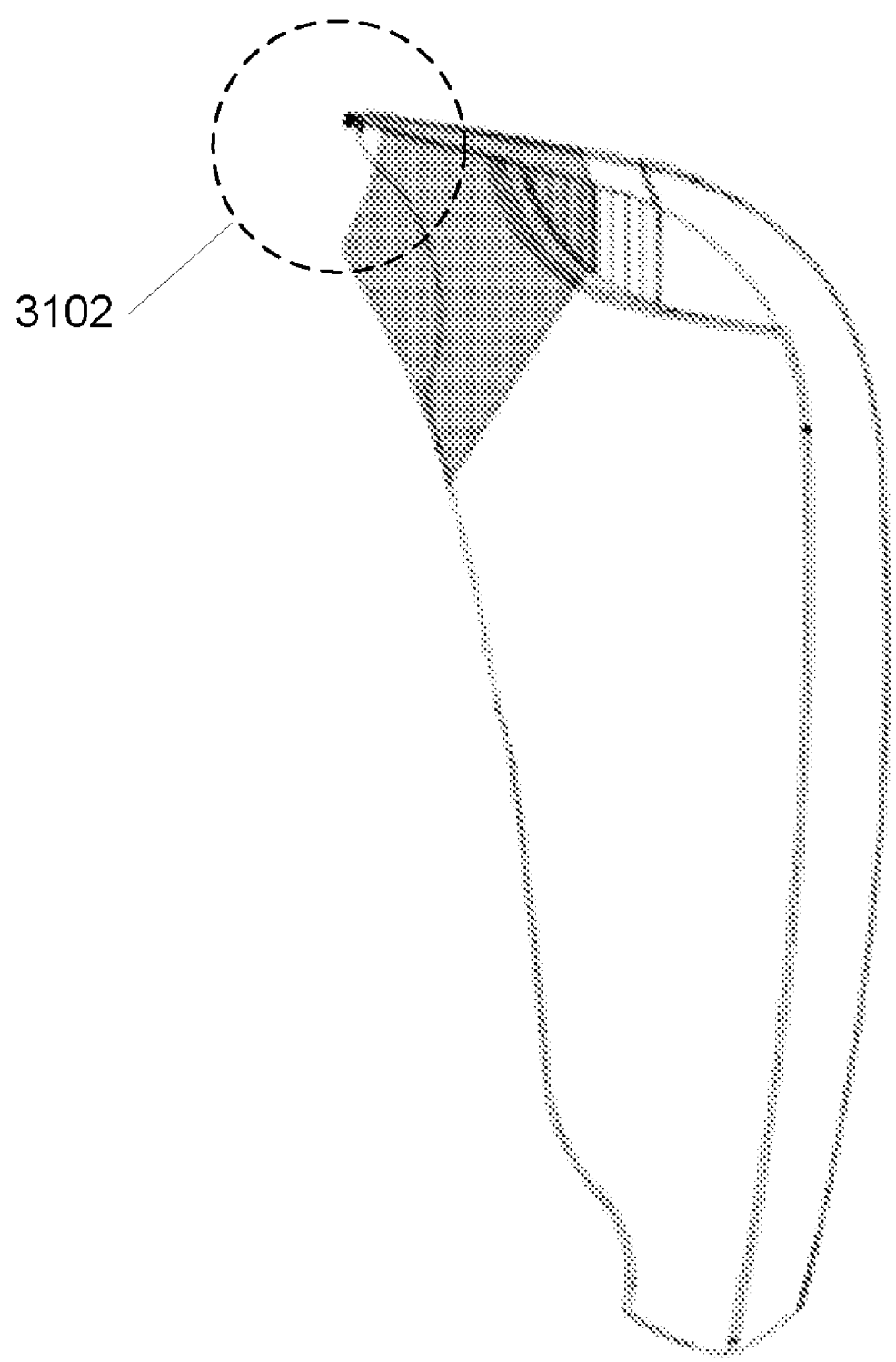

The shaded area of FIG. 31 illustrates an embodiment that comprises an increased "under bite" 3102, which can lead to softening of the pivot point.

Figure 32:
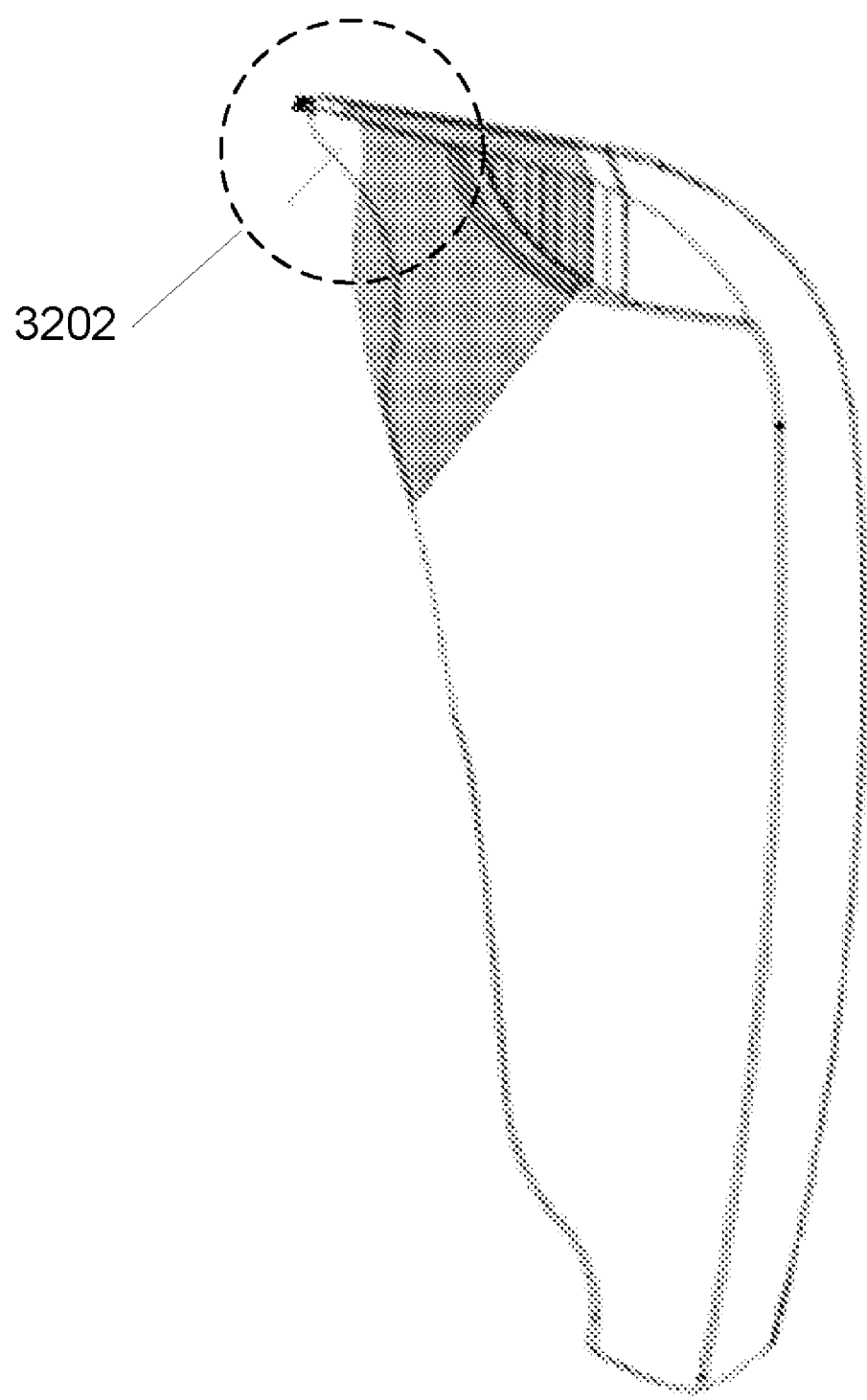

The shaded area of FIG. 32 illustrates another embodiment that comprises an increased "under bite" 3202, which can lead to a softening of the pivot point.

In one embodiment, the batteries and majority of weight of pen 2100 can be located near the tip of capsule 2202 (FIG. 22) near the duck bill shape 2602 (FIG. 26B), which minimizes torque against the fulcrum during tear collection and which minimizes gain on the user's neuromuscular feedback and subsequently reduces vibrations at the tip.

As noted above, auditory and visual feedback can be used to convey various states of the device. For example, an auditory, i.e., beep, and/or visual feedback, i.e., blinking or activated LED, can be used to indicate capsule 2202 has been properly interfaced with pen 2100 and has passed quality control tests to ensure proper electrical, fluidic and/or optical connections to TCI 2206. Also, upon wicking tears into pen 2100, an embedded light source, i.e., LED, can be configured to respond. An auditory indication can also be generated upon successful wicking of tears.

In certain embodiments, when tears bridge the energy transduction mechanism within TCI 2206, the LED can be configured to turn OFF and an audible noise can be emitted from pen 2100. In other embodiments, an LED can turn a certain color, e.g., green, when capsule 2202 is successfully inserted and can turn another color, e.g., red, when tears bridge the energy transduction mechanism. In this way, a user knows not to collect tears unless the light is ON, or the appropriate color. Similar feedback is possible when docking a Pen into an instrument or a time limit is approached for air exposure of the capsule.

Given such a prompt, a user who approaches a base unit with a stored pen with a used TCI card 2206 attached, will not see the LED illuminated. As such, the user will know not to use the pen without first replacing the disposable capsule 2202. This type of prompt is helpful for ensuring blood borne pathogen compliance in busy clinical settings. In another embodiment, the LED could be turned ON when tears cross the transduction mechanism within TCI card 2206.

Figure 33A:
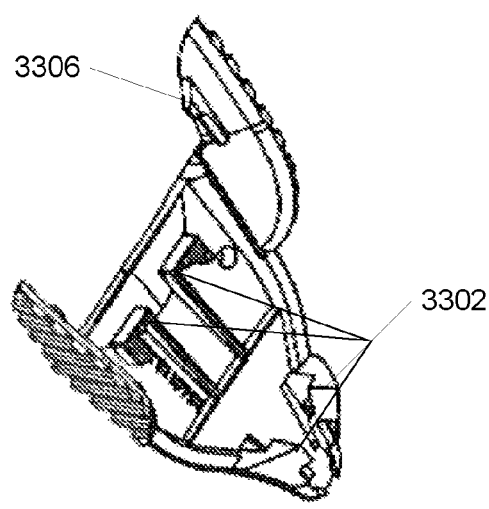
FIGS. 33A and B are diagrams illustrating an alternative embodiment of the capsule of FIG. 22.
Figure 33B:
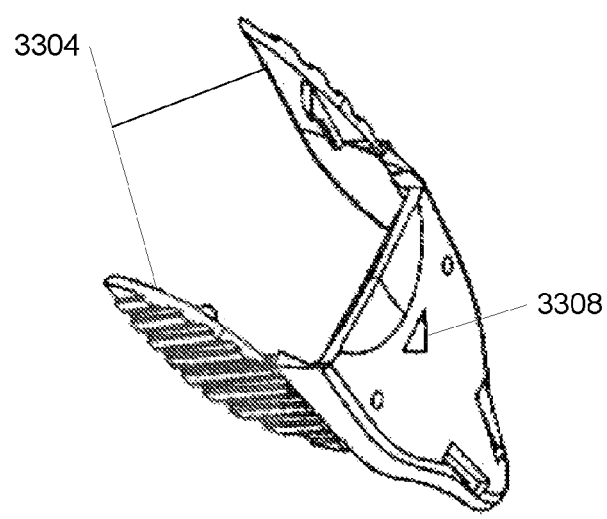

FIGS. 33A and B illustrate a slightly different capsule 2202. As can be seen, capsule 2202 comprises different shaped tabs 3302 and wings 3304. Also, a positive feature 3306 can be included in capsule 2202, which can be configured to mate with a corresponding negative feature in the pen body. It will also be understood that a negative feature can be included in capsule 2202 and corresponding positive feature in the pen body.

Moreover, a compression release mechanism 3308 can be included within capsule 2202 in order to provide safe and easy release of capsule 2202 from pen 2100. For example, since the user will likely have their fingers and or thumbs on wings 2204 while collecting a tear sample, this type of interaction cannot cause capsule 2202 to disengage form pen 2100. Thus, when positive feature 3306 is engaged with pen 2100, they must be configured so as to not allow capsule 2202 to disengage when pressure is applied to wings 3304. Release mechanism 3308 can then allow features 3306 to disengage when pressure is applied to mechanism 3308. Moreover, feature 3308 can be configured such that a slight downward pressure can cause capsule 2202 to disengage and slide forward out of pen 2100 for removal.

Figure 34A:
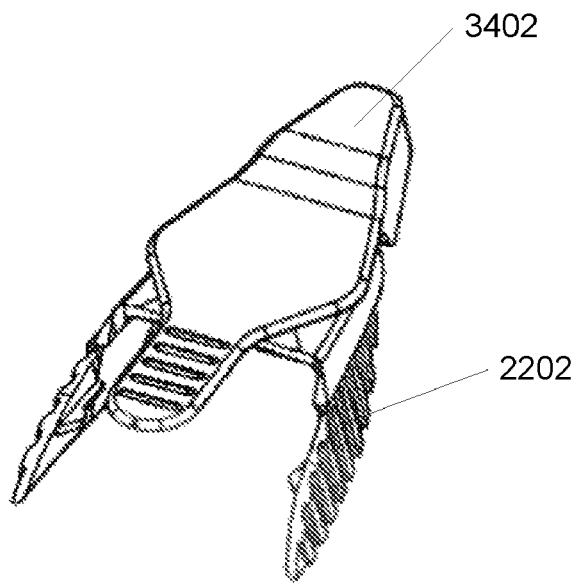
FIGS. 34A and B are diagrams illustrating a sheath configured to protect the capsule of FIGS. 22 and 33 before it is interfaced with the pen device, e.g., of FIG. 21.
Figure 34B:
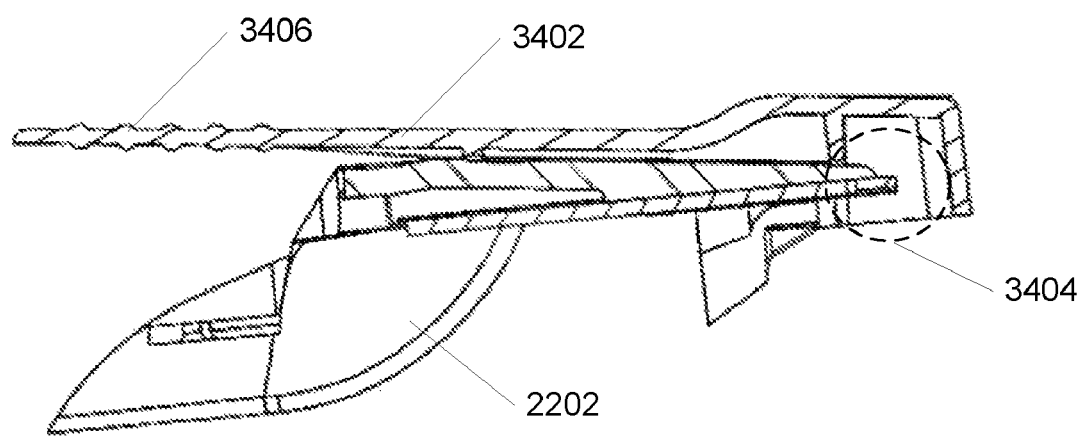

FIGS. 34A and B illustrate one example embodiment of a sheath 3402 that can be used in conjunction with capsule 2202 prior to capsule 2202 being inserted into pen 2100. As can be seen, sheath 3402 can encase capsule 2202 in such a manner as to prevent damage to recontamination of TCI 2206. For example, sheath 3402 can isolate the tip 3404 portion of TCI 2206 to ensure it is not damaged during handling and to ensure that it is not contaminated.

Sheath 3302 can comprise a tab 3306 that can allow sheath 3302 to be removed, i.e., by pulling forward on tab 3306.

As noted above, in certain embodiments, capsule 2202 can be removed and interface with a processing unit 606 so that the processing unit can determine the osmolarity of the sample fluid. In other embodiments, however, the entire pen 2100 can be interfaced with a processing unit 606. Pen 2100 can be configured to then transfer the relevant signals to processing unit 606 so that processing unit 606 can calculate the osmolarity. In other embodiments, pen 2100 can comprise the circuitry necessary to calculate the osmolarity on its own. In such embodiments, pen 2100 can still be configured to be interfaced with a processing, or base unit 606 so that the transduction data can be transferred and e.g., displayed, converted and/or stored.

The embodiments described above are generally related to systems and methods for detecting, or determining osmolarity for a fluid sample; however, it will be appreciated that the systems and methods described herein are not limited to the detection/determination of osmolarity. Rather, the systems and methods described herein can be employed to detect other parameters associated with a sample fluid. For example, in the embodiments described below, the systems and methods described herein can be used to detect any analyte of interest contained in the fluid sample. For example, the systems and methods described herein can be used to detect analytes such as proteins, peptides, and oligonucleotides. More specifically, the systems and methods described herein can be used to detect, or measure any immunoglobulin, such as Immunoglobulin E (IgE), which can be useful for testing for allergies, Immunoglobulin M (IgM), Immunoglobulin A (IgA), Immunoglobulin M (IgM), etc.

More broadly, the systems and methods described herein can be used to detect or measure various biomarkers in the sample fluid. For example, the systems and methods described herein can be used to detect biomarkers in tears, such as osmolarity, IgE, lactoferrin, cytokines, etc. For example, in certain embodiments, electrical signals produced by electrodes in sample region 806 can be used to detect analytes such as proteins. In other embodiments, however, optical detection methods can be used to detect analytes of interest. In general, any of various transduction techniques can be used to detect or measure an analyte of interest. For example, electrochemical, optoentropic, optomechanical, fluorescent, chemiluminescent, chromataographic, surface plasmon resonant (SPR) transduction methods can be used to detect analytes in a fluid sample incident on sample region 806. In other embodiments, nanobeads can be used to detect analyte of interest in the sample fluid. For example, the nanobeads can be coated with a chemical that changes fluorescence based on the amount of the target analyte present in the sample fluid. In other embodiments, the nanobeads can be coated with a biological substance that binds to the analyte of interest. Light can then be used to illuminate the beads and detect the presence of the analyte, e.g., using SPR or by detecting fluorescence, luminescence, or other changes in the energy properties of the sample region. Other transduction mechanisms such as electrochemical including potentiometric, amperometric, capacitance, and impedance spectroscopy, cyclic voltammery, pulse voltammery, etc., transduction methods can be used in conjunction with the electrodes within the sample region. Enzyme modified electrochemical redox reactions, such as horseradish peroxidase labels, gold nanoparticle labels, and other electrochemically active labels can be used within the transduction mechanism. Further embodiments can include measuring changes in potentiometric conductive polymers, such as polypyrrole, after exposure to tear fluid.

Conductive polymers and the other transduction systems described herein can be incorporated directly into the sample region of the substrate in order to mitigate the effects of evaporation on an open system.

In addition to physically locate the transduction system within the collection interface, two other methods of mitigating evaporation during measurement of analytes of interest include a sealing cap for the tear collection interface, as well as the use of software to normalize the analyte of interest against the osmolarity of the sample. The cap could be comprised of an interference fitted plastic, or gasketed seal, much like a normal pen cap, which slides over both the vent hole of the substrate and channel opening 1402. The cap design could allow for a very small displacement of air, as the movement of fluid within the channel is undesired. For example, vent holes that are carved along the outside of the pen cap could terminate just prior to sealing such that sufficient mechanical stability is achieved while minimizing the air displacement.

Figure 19:
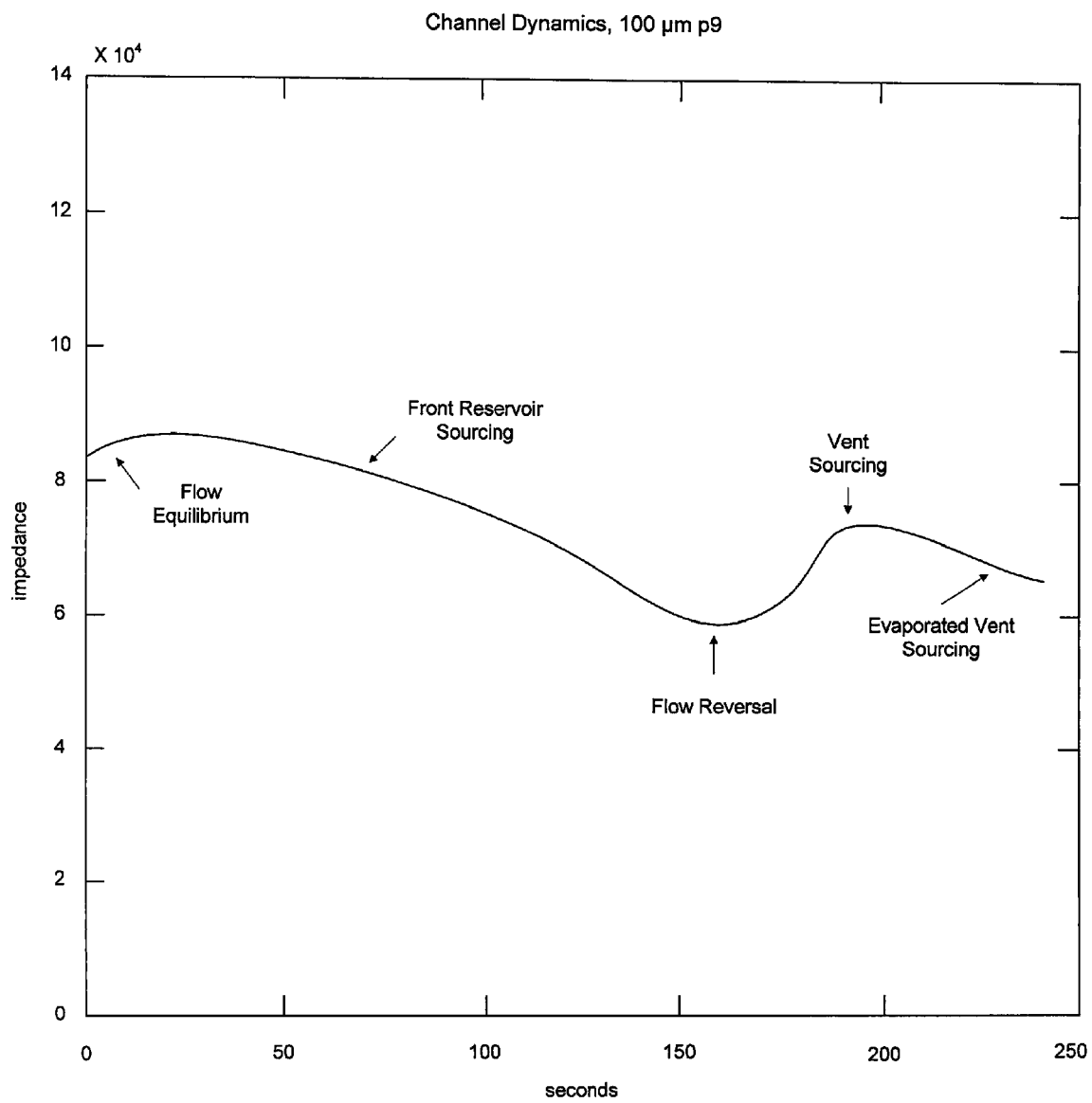
FIG. 19 is a graph illustrating the change in osmolarity over time within a receiving substrate.

Osmolarity normalization can be calculated to compensate for the intrinsic evaporation while the tears are within the patient's tear film, as well as for osmolarity changes during residence within the channel. During measurement of analytes of interest, biochemical assays often require incubation times that can be significantly longer than the times needed to measure the impedance of the tear fluid. FIG. 19 demonstrates a typical change in osmolarity over time within a receiving substrate as measured by a four-point impedance method. The initial transient, within the first 10 seconds, sees the impedance increase as a result of the equilibration (slowing) of the tear fluid being pulled into the capillary channel. Often, a small volume of residual tear remains outside of the substrate immediately following tear collection. As these tears are exposed to the environment with a large surface area, these tears are of higher osmolarity than the tears that originally populated the channel. Continual capillary action draws this higher concentration fluid into the channel and mixes the fluids, gradually decreasing the impedance of the fluid as the concentration changes. As the residual tear source is lost, the flow of the fluid begins to slow again, e.g., about 140 seconds in, increasing the impedance. If the vent hole contains a reservoir of fluid, it is typically hypoosmolar at the base of the column, the fluid unexposed to the air. Once the vent starts sourcing the fluid back into the channel, the hypoosmolar fluid lowers the concentration of the fluid and increases the impedance. After all sources have been emptied, the impedance drops in a near-linear fashion, indicative of steady evaporation.

Figure 20:
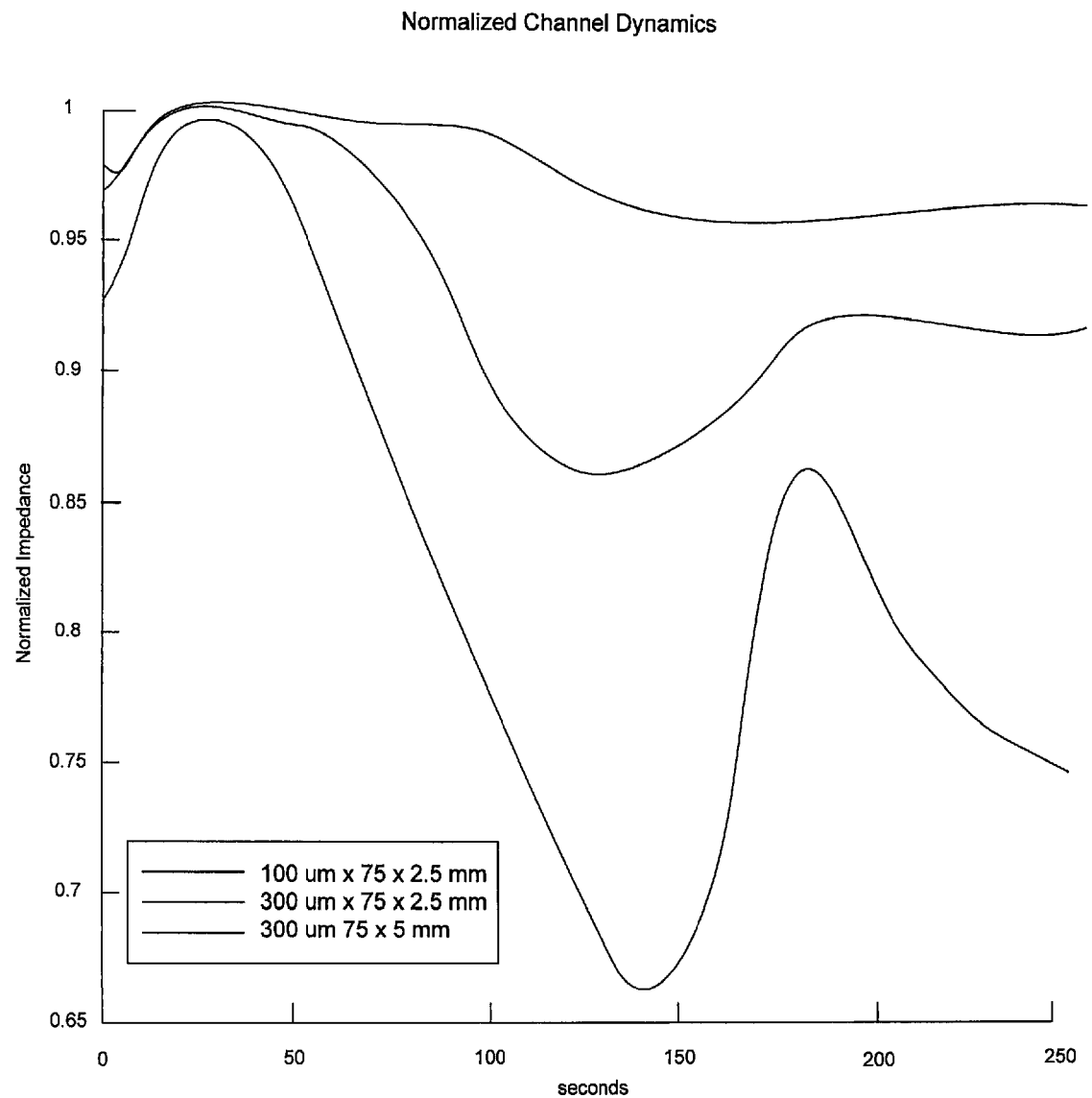
FIG. 20 is a graph illustrating the change in osmolarity over time for three different tear collection interfaces.

FIG. 20 exhibits these dynamics across three different tear collection interface geometries. The smaller the channel, the larger the gain of the dynamics. As can be seen, a 100 µm wide, by 75 µm deep, by 2.5 mm long sinusoidal channel constructed from polyester PSA thermally bonded to polycarbonate, has the greatest percent change in osmolarity during incubation, with about a 34% change over 150 seconds. A 300 µm wide, by 75 µm deep, by 5 mm long channel sees only a few percent change over the time of incubation.

The transduction of analytes of interest can be normalized against these dynamics. For instance, an instantaneous potentiometric measurement can be normalized against the ratio of the initial steady state value, e.g., around 10 seconds, vs. the instantaneous impedance at the time of measurement as one of the methods of normalization. Integral amperometric methods can be normalized against the average of the displacement of the impedance curve. In general, many normalizations can be made to adjust the reported level of analyte of interest in order to improve the standard of care.

The systems and methods described herein have been described above in terms of exemplary embodiments so that an understanding of the present invention can be conveyed. Any embodiment described herein as "exemplary" is not necessarily to be construed as preferred or advantageous over other embodiments. Moreover, there are many configurations for the systems and associated components not specifically described herein but with which the present invention is applicable. The systems and methods described herein should therefore not be seen as limited to the particular embodiments described herein, but rather, it should be understood that the present invention has wide applicability. For example, in addition to tear film and osmolarity, the systems and methods described herein can be used for any fluid, e.g., serum, and to detect a variety of parameters including osmolarity and the presence, or amount of an analyte of interest. All modifications, variations, or equivalent arrangements and implementations that are within the scope of the attached claims should therefore be considered within the scope of the invention.

What is claimed is:

1. A fluid collection device, comprising:
 a body comprising a capsule interface; and
 a capsule configured to interface with the body via the capsule interface and configured to hold a sample receiving chip, the sample receiving chip comprising:
 a substrate that receives an aliquot volume of a sample fluid, wherein the substrate is operatively shaped to receive the aliquot volume of sample fluid through capillary action,
 a sample region of the substrate, sized such that the aliquot volume of the sample fluid is sufficient to operatively cover a portion of the sample region, whereupon energy properties of the sample fluid can be transduced to produce a sample fluid reading.

2. The fluid collection device of claim 1, wherein the capsule comprises tabs configured to hold the sample receiving chip in place.

3. The collection device of claim 1, wherein the capsule interface comprises fluidic connections between the sample receiving chip and the body.

4. The collection device of claim 1, wherein the capsule interface comprises electrical connections between a transduction mechanism included in the sample receiving chip and circuitry included within the body.

5. The collection device of claim 4, wherein the body further comprises circuitry configured to produce the sample fluid reading.

6. The collection device of claim 4, wherein the body further comprises a connector configured to interface the body with a processing unit and electrical and fluidic interfaces from the capsule-body interface, through the body and to the connector.

7. The collection device of claim 1, wherein the body further comprises a rotational feature that converts a gross rotation of the collection device into a fine linear translation of a tip of the sample receiving chip.

8. The collection device of claim 1, wherein the capsule is further configured to hold the sample receiving chip such that a tip portion of the sample receiving chip extends out beyond the end of the capsule sufficiently to allow the sample receiving chip to receive the aliquot volume of a sample fluid.

9. The collection device of claim 8, wherein the sample fluid is tears collected from the meniscus, and wherein the tip of the sample receiving chip comprises a width and shape sufficient to soften the entrance of the tip into the meniscus during tear collection.

10. The collection device of claim 9, wherein the width of the tip is approximately 3 millimeters.

11. The collection device of claim 10, wherein the tip extends approximately 0.5 millimeters.

12. The sample receiving chip of claim 1, wherein the substrate is operatively shaped to receive the aliquot volume of sample fluid at the edge of the substrate.

13. The collection device of claim 12, wherein the capsule interface comprises a vent configured to enable the sample receiving chip to receive the aliquot volume of sample fluid at the edge of the substrate.

14. The collection device of claim 1, wherein the substrate is operatively shaped to act as a fluid collection interface.

15. The collection device of claim 1, wherein the sample region includes a plurality of electrodes disposed to contact the sample fluid.

16. The collection device of claim 15, wherein the plurality of electrodes is arranged in a row and column array.

17. The collection device of claim 16, further comprising a plurality of conductive connection lines coupled to the plurality of electrodes, wherein the conductive connection lines provide means for transferring energy to and from the sample fluid.

18. The collection device of claim 1, wherein the sample fluid includes bodily fluid.

19. The collection device of claim 18, wherein the bodily fluid is a tear film.

20. The collection device of claim 1, wherein the sample fluid reading indicates osmolarity of the sample fluid.

21. The collection device of claim 1, wherein the body further comprises a visual indicator configured to indicate when the capsule is properly interfaced with the body.

22. The collection device of claim 1, wherein the body further comprises a visual indicator configured to indicate when the sample fluid is being transduced.

23. The collection device of claim 1, wherein the body further comprises an audible indicator configured to indicate when the capsule is properly interfaced with the body.

24. The collection device of claim 1, wherein the body further comprises an audible indicator configured to indicate when the sample fluid is being transduced.

* * * * *